US007202366B2

(12) United States Patent
Nag et al.

(10) Patent No.: US 7,202,366 B2
(45) Date of Patent: *Apr. 10, 2007

(54) HETEROCYCLIC ANALOGS OF DIPHENYLETHYLENE COMPOUNDS

(75) Inventors: Bishwajit Nag, Union City, CA (US); Debendranath Dey, Fremont, CA (US); Satyanarayana Medicherla, Cupertino, CA (US); Partha Neogi, Fremont, CA (US)

(73) Assignee: Theracos, Inc., Sunnyvale, CA (US)

( * ) Notice: Subject to any disclaimer, the term of this patent is extended or adjusted under 35 U.S.C. 154(b) by 279 days.

This patent is subject to a terminal disclaimer.

(21) Appl. No.: 10/808,519

(22) Filed: Mar. 25, 2004

(65) Prior Publication Data

US 2004/0186299 A1    Sep. 23, 2004

Related U.S. Application Data

(63) Continuation of application No. 09/843,167, filed on Apr. 27, 2001, now Pat. No. 7,105,552, which is a continuation-in-part of application No. 09/785,554, filed on Feb. 20, 2001, now abandoned, which is a continuation-in-part of application No. 09/591,105, filed on Jun. 9, 2000, now abandoned, which is a continuation-in-part of application No. 09/287,237, filed on Apr. 6, 1999, now Pat. No. 6,331,633, which is a continuation-in-part of application No. 09/074,925, filed on May 8, 1998, now Pat. No. 6,245,814.

(51) Int. Cl.
*A61K 31/41* (2006.01)
*C07D 277/60* (2006.01)

(52) U.S. Cl. ............. 548/183; 548/227; 548/226; 548/318.5; 514/369; 514/376; 514/389; 514/439; 514/441

(58) Field of Classification Search ............ 54/183, 54/227, 226, 318.5
See application file for complete search history.

(56) References Cited

U.S. PATENT DOCUMENTS

| | | | |
|---|---|---|---|
| 3,609,183 A | 9/1971 | DeWald et al. |
| 3,683,009 A | 8/1972 | Middleton |
| 3,846,398 A | 11/1974 | Hirschmann et al. |
| 4,092,335 A | 5/1978 | Gruszecki et al. |
| 4,217,366 A | 8/1980 | Kikumoto et al. |
| 4,271,186 A | 6/1981 | Forster et al. |
| 4,284,637 A | 8/1981 | Kikumoto et al. |
| 4,297,429 A | 10/1981 | Kanada et al. |
| 4,310,534 A | 1/1982 | Kikumoto et al. |
| 4,312,855 A | 1/1982 | Grand |
| 4,326,055 A | 4/1982 | Loeliger |
| 4,716,905 A | 1/1988 | Schmued |
| 4,866,086 A | 9/1989 | Boyle et al. |
| 4,929,635 A | 5/1990 | Coquelet et al. |
| 4,940,707 A | 7/1990 | Klaus et al. |
| 5,087,637 A | 2/1992 | Janssen et al. |
| 5,158,966 A | 10/1992 | Lafferty et al. |
| 5,162,337 A | 11/1992 | Elbrecht et al. |
| 5,171,753 A | 12/1992 | Munson, Jr. et al. |
| 5,189,056 A | 2/1993 | Orlando et al. |
| 5,246,936 A | 9/1993 | Treacy et al. |
| 5,250,562 A | 10/1993 | Klaus et al. |
| 5,314,693 A | 5/1994 | Suga |
| 5,378,705 A | 1/1995 | Klaus et al. |
| 5,409,953 A | 4/1995 | Pettit et al. |
| 5,430,062 A | 7/1995 | Cushman et al. |
| 5,494,932 A | 2/1996 | Cardin et al. |
| 5,521,160 A | 5/1996 | Chucholowski et al. |
| 5,525,632 A | 6/1996 | Obsumi et al. |
| 5,532,129 A | 7/1996 | Heller |
| 5,559,151 A | 9/1996 | Adorante et al. |
| 5,565,191 A | 10/1996 | Raspanti |
| 5,565,322 A | 10/1996 | Heller |
| 5,569,786 A | 10/1996 | Pettit et al. |
| 5,583,128 A | 12/1996 | Bhatnagar |
| 5,589,506 A | 12/1996 | Hashimoto et al. |
| 5,672,625 A | 9/1997 | Cardin et al. |
| 5,674,906 A | 10/1997 | Hatanaka et al. |
| 5,705,530 A | 1/1998 | Adorante et al. |
| 5,716,928 A | 2/1998 | Benet et al. |
| 5,731,353 A | 3/1998 | Ohsumi et al. |
| 5,733,909 A | 3/1998 | Black et al. |
| 5,767,268 A | 6/1998 | Chucholowski et al. |
| 5,770,620 A | 6/1998 | Mjalli et al. |
| 5,827,898 A | 10/1998 | Khandwala et al. |
| 5,972,973 A | 10/1999 | Whitcomb |
| 5,985,884 A | 11/1999 | Lohray et al. |
| 5,990,139 A | 11/1999 | Yano et al. |

(Continued)

FOREIGN PATENT DOCUMENTS

EP    32128    6/1981

OTHER PUBLICATIONS

Sohda et al. "Antiulcer Activity of 5-benzylthiazolidine-2,4-dione derivatives" *Chem. Pharm. Bull.* 31:2 (1983) 560-9.

(Continued)

*Primary Examiner*—Samuel Barts
(74) *Attorney, Agent, or Firm*—Jones Day

(57) ABSTRACT

Novel diphenylethylene compounds and derivatives thereof containing thiazolidinedione or oxazolidinedione moieties are provided which are effective in lowering blood glucose level, serum insulin, triglyceride and free fatty acid levels in animal models of Type II diabetes. In contrast to previously reported thiazolidinedione compounds, known to lower leptin levels, the present compounds increase leptin levels and have no known liver toxicity. The compounds are disclosed as useful for a variety of treatments including the treatment of inflammation, inflammatory and immunological diseases, insulin resistance, hyperlipidemia, coronary artery disease, cancer and multiple sclerosis.

12 Claims, 14 Drawing Sheets

U.S. PATENT DOCUMENTS

| | | | |
|---|---|---|---|
| 6,008,237 | A | 12/1999 | Sahoo et al. |
| 6,011,031 | A | 1/2000 | Lohray et al. |
| 6,011,036 | A | 1/2000 | Lohray et al. |
| 6,030,973 | A | 2/2000 | Lohray et al. |
| 6,034,110 | A | 3/2000 | Nagpal et al. |
| 6,046,202 | A | 4/2000 | Antonucci et al. |
| 6,046,222 | A | 4/2000 | Antonucci et al. |
| 6,080,765 | A | 6/2000 | Ikeda et al. |
| 6,103,742 | A | 8/2000 | Ikeda et al. |
| 6,107,323 | A | 8/2000 | Tamura et al. |
| 6,110,948 | A | 8/2000 | Momose et al. |
| 6,110,951 | A | 8/2000 | Pershadsingh et al. |
| 6,114,526 | A | 9/2000 | Lohray et al. |
| 6,117,893 | A | 9/2000 | Fujita et al. |
| 6,121,294 | A | 9/2000 | Ikeda et al. |
| 6,121,295 | A | 9/2000 | Ikeda et al. |
| 6,130,216 | A | 10/2000 | Antonucci et al. |
| 6,133,293 | A | 10/2000 | Ikeda et al. |
| 6,133,295 | A | 10/2000 | Ikeda et al. |
| 6,245,814 | B1 | 6/2001 | Nag et al. |
| 6,331,633 | B1 | 12/2001 | Neogi et al. |
| 6,624,197 | B1 | 9/2003 | Nag et al. |
| 2002/0025975 | A1 | 2/2002 | Nag et al. |
| 2003/0181494 | A1 | 9/2003 | Neogi et al. |

OTHER PUBLICATIONS

Giles et al. "Regiospecific Reduction of 5-benzylidene-2,4-thiazolidinediones and 4-oxo-2-thiazolidinethiones Using Lithium Borohydride in Pyridine and Tetrahydrofuran" *Tetrahedron* 56:26 (2000) 4531-4537.

Myaoka et al. "Preparation of 2,4-Dioxo-1,2,3,4-Tetrahydroquinazoline Derivatives Having Blood Sugar-Lowering and Aldose Reductase-Inhibiting Activity" *Japan Kokai Tokkyo Koho* (1996).

Hulin et al. "Novel Thiazolidone-2,4-Diones as Patent Euglycemic Agents" *J. Med. Chem.* 35:10 (1992) 1853-64.

Pettit et al. "Isolation, Structure, Synthesis and Antimitotic Properties of Combretastttins B-3 and B-4 from Combretum Caffrum" *Journal of Natural Products* 51:3 (1988) 517-527.

Green, Richard H. "Syntheses of Differanisole A" *Tetrahedron Letters* 38:26 (1997) 4697-4700.

Reddy et al. "From Styrenes to Enanitopure α-Arylglycines in Two Steps" *J. Am. Chem. Soc.* 120 (1998) 1207-1217.

Momose et al. "Studies on Antidiabetic Agents. X.[1)] Synthesis and Biological Activities of Pioglitazone and Related Compounds" *Chem. Pharm. Bull.* 39(6) (1991) 1440-1445.

Cantello et al. "[[ω-(Heterocyclylamino)alkoxy]benzyl]-2,4-thiazolidinediones as Potent Antihyperglycemic Agents" *J. Med. Chem.* 37 (1994) 3977-3985.

Sohda et al. "Studies on Antidiabetic Agents. XII.[1)] Synthesis and Activity of the Metabolites of (±)-5-[-p-[2-(5-Ethyl-2-pyridyl)ethoxy]benzyl]-2,4-thiazolidinedione (Pioglitazone)" *Chem. Pharm. Bull.* 43(12) (1995) 2168-2172.

Willson et al. "The Structure-Activity Relationship between Peroxisome Proliferator-Activated Receptor γ Agonism and the Antihyperglycemic Activity of Thiazolidinediones" *J. Med. Chem.* 39 (1996) 665-668.

Tanis et al. "Synthesis and Biological Activity of Metabolites of the Antidiabetic; Antihyperglycemic Agent Pioglitazone" *J. Med. Chem.* 39 (1996) 5053-5063.

Shinkai et al. "Isoxazolidine-3,5-dione and Noncyclic 1,3-Dicarbonyl Compounds as Hypoglycemic Agents" *J. Med. Chem.* 41 (1998) 1927-1933.

Lohray et al. "Novel Euglycemic and Hypolipidemic Agents" *J. Med. Chem.* 41(1998)1619-1630.

Reddy et al. "Novel Antidiabetic and Hypolipidemic Agents. 5. Hydroxyl versus Benzyloxy Containing Chroman Derivatives" *J. Med. Chem.* 42 (1999) 3265-3278.

Turnbow MA, Smith LK, Garner CW. The oxazolidinedione CP-92,768-2 partially protects insulin receptor substrate-1 from dexamethasone down-regulation in 3T3-L1 adipocytes. Endocrinology. Apr. 1995; 136(4):1450-8.

Yoshioka T, Fujita T, Kanai T, Aizawa Y, Kurumada T, Hasegawa K, Horikoshi H. Studies on hindered phenols and analogues. 1. Hypolipidemic and hypoglycemic agents with ability to inhibit lipid peroxidation, J Med Chem. Feb. 1989; 32(2):421-8.

Zask A, Jirkovsky I, Nowicki JW, McCaleb ML. Synthesis and antihyperglycemic activity of novel 5-(naphthalenylsulfonyl)-2,4-thiazolidinediones. J Med Chem. 33:5 (1990) 1418-23.

Sohda T, Mizuno K, Momose Y, Ikeda H, Fujita T, Meguro K. Studies on antidiabetic agents. 11. Novel thiazolidinedione derivatives as potent hypoglycemic and hypolipidemic agents. J Med Chem. Jul. 10, 1992;35(14):2617-26.

Hulin B, Newton LS, Lewis DM, Genereux PE, Gibbs EM, Clark DA. Hypoglycemic activity of a series of alpha-alkylthio and alpha-alkoxy carboxylic acids related to ciglitazone. J Med Chem. Sep. 27, 1996; 39(20):3897-907.

Arakawa K, Inamasu M, Matsumoto M, Okumura K, Yasuda K, Akatsuka H, Kawanami S, Watanabe A, Homma K, Saiga Y, Ozeki M, Iijima I. Novel benzoxazole 2,4-thiazolidinediones as potent hypoglycemic agents. Synthesis and structure-activity relationships. Chem Pharm Bull (Tokyo). Dec. 1997; 45(12):1984-93.

Dow et al. "Benzyloxazolidine-2,4-diones as Potent Hypoglycemic Agents" *J. Med. Chem.* 1991 vol. 34 1538-1544.

Sohda et al. "Studies on Antidiabetic Agents. II. Synthesis of 5-[4-(1-Methylcyclohexylmethoxy)-benzyl]thiazolidine-2,4-dione (ADD-3878) and Its Derivatives" *Chemical & Pharmaceutical Bulletin* 30:10 (Oct. 1982) pp. 3580-3600.

Abstract—Gibbs et al. "The Benzyloxazolidinedione, CP-92768, is a Potent Antidiabetic Agent In Vivo and In Vitro" *Diabetes* 42 (Suppl. I) 1993 p. 207A.

U.S. Appl. No. 10/690,844, filed Oct. 23, 2003.

Glucose in db/db and ob/ob Diabetic Mice db/db Mice ob/ob Mice

Time Course

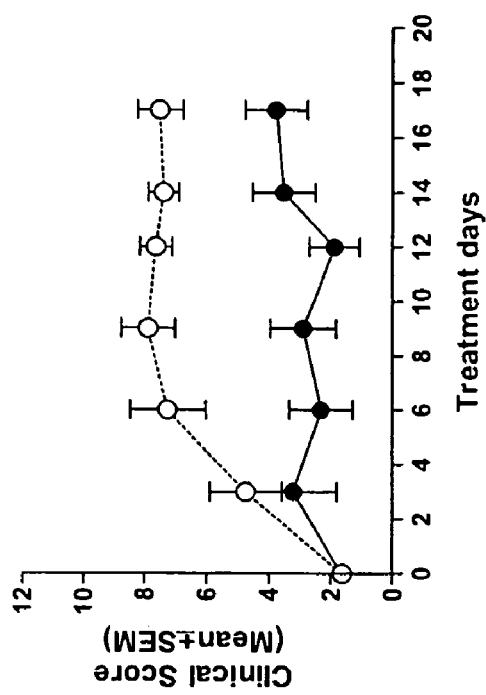
FIG. 13B. Clinical Score
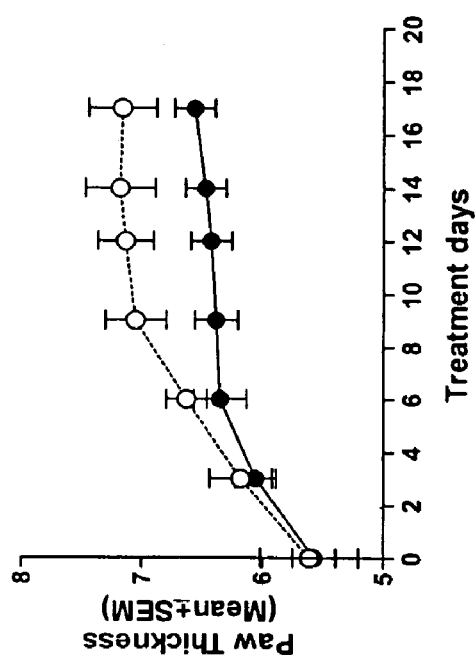
FIG. 13D. Paw Thickness
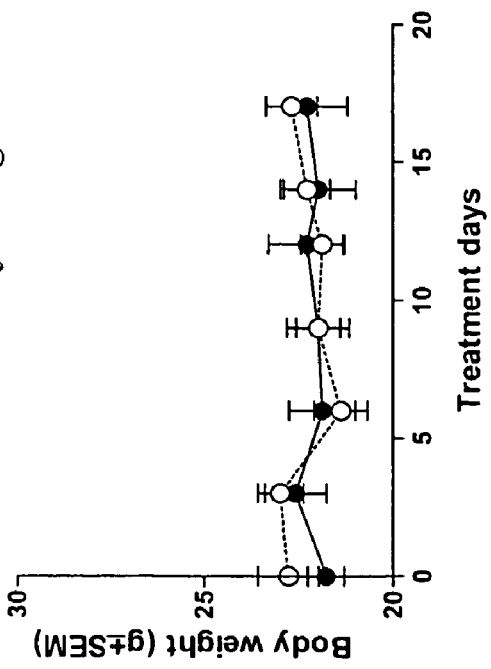
FIG. 13A. Body Weight
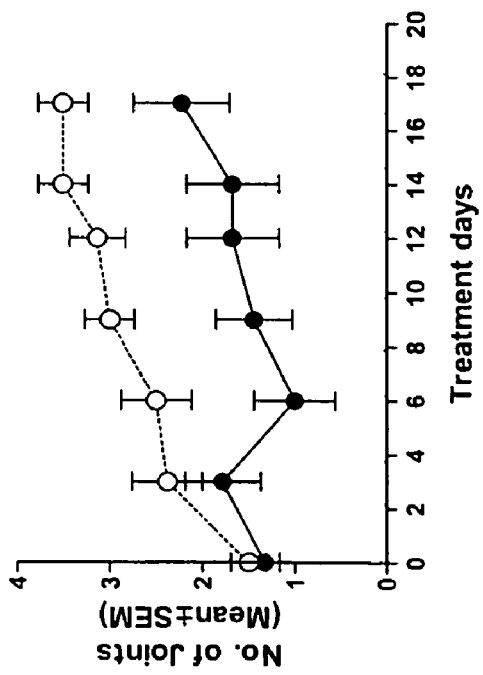
FIG. 13C. Joints Affected
--○-- Vehicle (10% PEG)
—●— CPD VIII (50 mg/kg)
n=8-9

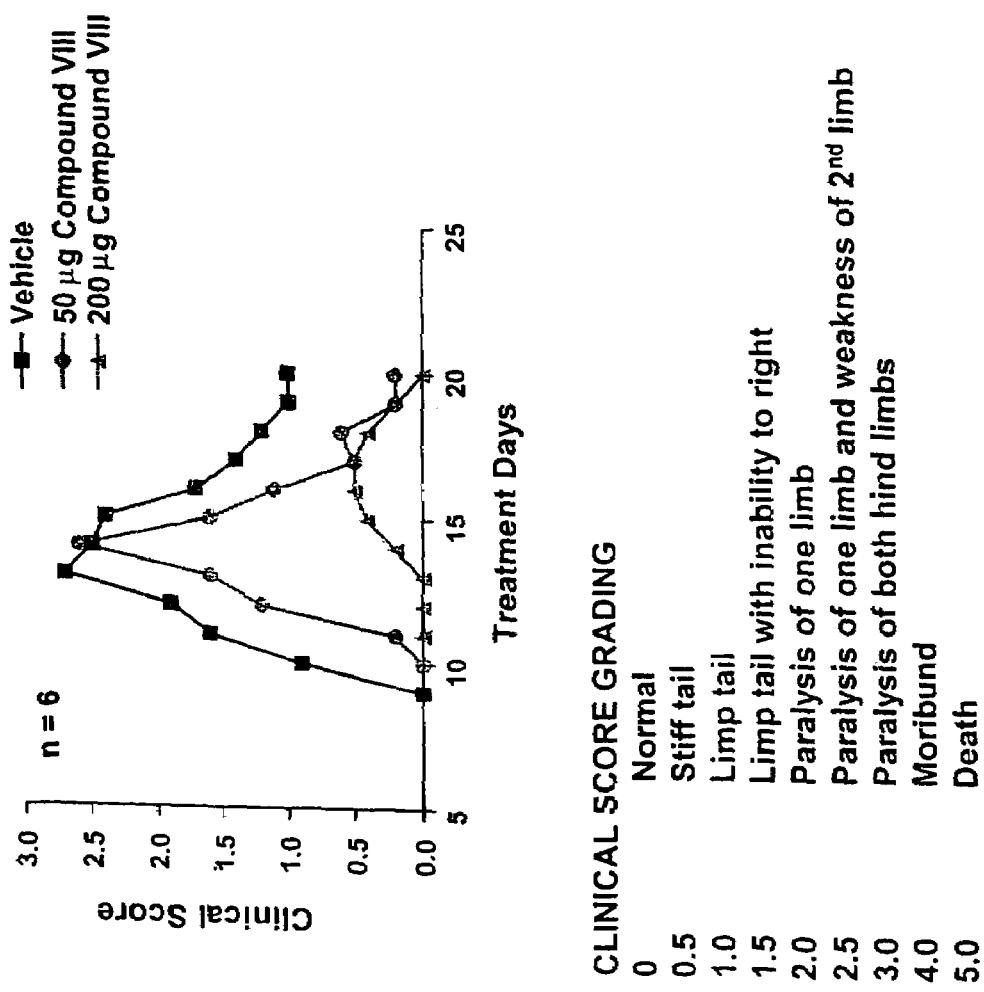
Fig. 14 Treatment of EAE in SJL/J Mice with Compound VIII

HETEROCYCLIC ANALOGS OF DIPHENYLETHYLENE COMPOUNDS

CROSS REFERENCE TO RELATED APPLICATIONS

This is a continuation of U.S. Ser. No. 09/843,167, filed Apr. 27, 2001 now U.S. Pat No. 7,105,552, which is further a continuation-in-part of U.S. Ser. No. 09/785,554, filed Feb. 20, 2001 now abandoned, which is a continuation-in-part of U.S. Ser. No. 09/591,105, filed on Jun. 9, 2000 now abandoned, which is a continuation-in-part of Ser. No. 09/287,237, filed on Apr. 6, 1999 now U.S. Pat. No. 6,331,633, which is a continuation-in-part of Ser. No. 09/074,925, filed on May 8, 1998 now U.S. Pat. No. 6,245,814, the disclosures of said earlier applications being incorporated, in their entirety, herein by reference.

BACKGROUND OF THE INVENTION

The present application is directed to novel compounds formed by chemically coupling diphenylethylene compounds and derivatives thereof with thiazolidine or oxazolidine intermediates. These compounds are effective for providing a variety of useful pharmacological effects. For example, the compounds are useful in lowering blood glucose, serum insulin and triglyceride levels in animal models of type II diabetes. Surprisingly, these compounds have been found to increase the leptin level and have no liver toxicity.

Furthermore, these compounds are useful for treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines and cyclooxygenase such as TNF-alpha, IL-1, IL-6 and/or COX-2.

The causes of type I and type II diabetes are yet unknown, although both genetics and environment seem to be major factors. Insulin dependent type I and non-insulin dependent type II are the types which are known. Type I is an autoimmune disease in which the responsible autoantigen is still unknown. Patients of type I need to take insulin parenterally or subcutaneously to survive. However, type II diabetes, the more common form, is a metabolic disorder resulting from the body's inability to make a sufficient amount of insulin or to properly use the insulin that is produced. Insulin secretion and insulin resistance are considered the major defects, however, the precise genetic factors involved in the mechanism remain unknown.

Patients with diabetes usually have one or more of the following defects:

Less production of insulin by the pancreas;

Over secretion of glucose by the liver;

Independent of the glucose uptake by the skeletal muscles;

Defects in glucose transporters, desensitization of insulin receptors; and

Defects in the metabolic breakdown of polysaccharides.

Other than the parenteral or subcutaneous application of insulin, there are about 4 classes of oral hypoglycemic agents used.

| Class | Approved Drugs | Mechanisms of | Limitations |
|---|---|---|---|
| Sulfonylurea | 4 (1st generation) and 2 (2nd generation) | acts on pancreas to release more insulin | development of resistance |
| Biguanides | Metformin | reduces glucose production by liver; improves insulin sensitivity | liver problems, lactic acidosis |
| Alpha-glucosidase inhibitor | Acarbose | interferes with digestive process; reduces glucose absorption | only useful at post-prandial level |
| Thiazolidinedione | Troglitazone (withdrawn) rosiglitazone pioglitazone | reduce insulin resistancy | "add-on" with insulin; not useful for people with heart and liver disease |

As is apparent from the above table, each of the current agents available for use in treatment of diabetes has certain disadvantages. Accordingly, there is a continuing interest in the identification and development of new agents, particularly, water soluble agents which can be orally administered, for use in the treatment of diabetes.

The thiazolidinedione class listed in the above table has gained more widespread use in recent years for treatment of type II diabetes, exhibiting particular usefulness as insulin sensitizers to combat "insulin resistance", a condition in which the patient becomes less responsive to the effects of insulin. However, the known thiazolidinediones are not effective for a significant portion of the patient population. In addition, the first drug in this class to be approved by the FDA, troglitazone, was withdrawn from the market due to problems of liver toxicity. Thus, there is a continuing need for nontoxic, more widely effective insulin sensitizers.

Pharmaceutical compositions and methods utilizing thiazolidinediones are described in U.S. Pat. Nos. 6,133,295; 6,133,293; 6,130,216; 6,121,295; 6,121,294; 6,117,893; 6,114,526; 6,110,951; 6,110,948; 6,107,323; 6,103,742; 6,080,765; 6,046,222; 6,046,202; 6,034,110; 6,030,973; RE36,575; 6,011,036; 6,011,031; 6,008,237; 5,990,139; 5,985,884; 5,972,973 and others.

As indicated above, the present invention is also concerned with treatment of immunological diseases or inflammation, notably such diseases as are mediated by cytokines or cyclooxygenase. The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and providing the necessary "help" for T cell stimulation and proliferation. Most importantly macrophages make IL 1, IL 12 and TNFα all of which are potent pro-inflammatory molecules and also provide help for T cells. In addition, activation of macrophages results in the induction of enzymes, such as cyclooxygenase II (COX-2), inducible nitric oxide synthase (iNOS) and production of free radicals capable of damaging normal cells. Many factors activate macrophages, including bacterial products, superantigens and interferon gamma (IFNγ). It is believed that phosphotyrosine kinases (PTKs) and other undefined cellular kinases are involved in the activation process.

Macrophages take up and break down antigens into small fragments. These fragments then associate with the major histocompatibility complex II (MHC II). This complex of antigen fragments and MHC II is recognized by the T cell receptor. In association with appropriate co-stimulatory signals this receptor-ligand interaction leads to the activation and proliferation of T cells. Depending on the route of administration of antigen, their dose and the conditions under which macrophages are activated, the immune response can result in either B cell help and antibody production or on the development of cell mediated response. Since macrophages are sentinel to the development of an immune response, agents that modify their function, specifically their cytokine secretion profile, are likely to determine the direction and potency of the immune response.

Cytokines are molecules secreted by immune cells that are important in mediating immune responses. Cytokine production may lead to the secretion of other cytokines, altered cellular function, cell division or differentiation. Inflammation is the body's normal response to injury or infection. However, in inflammatory diseases such as rheumatoid arthritis, pathologic inflammatory processes can lead to morbidity and mortality. The cytokine tumor necrosis factor-alpha (TNF-alpha) plays a central role in the inflammatory response and has been targeted as a point of intervention in inflammatory disease. TNF-alpha is a polypeptide hormone released by activated macrophages and other cells. At low concentrations, TNF-alpha participates in the protective inflammatory response by activating leukocytes and promoting their migration to extravascular sites of inflammation (Moser et al., J Clin Invest, 83:444–55, 1989). At higher concentrations, TNF-alpha can act as a potent pyrogen and induce the production of other pro-inflammatory cytokines (Haworth et al., Eur J Immunol, 21:2575–79, 1991; Brennan et al., Lancet, 2:244–7, 1989). TNF-alph also stimulates the synthesis of acute-phase proteins. In rheumatoid arthritis, a chronic and progressive inflammatory disease affecting about 1% of the adult U.S. population, TNF-alpha mediates the cytokine cascade that leads to joint damage and destruction (Arend et al., Arthritis Rheum, 38:151–60, 1995). Inhibitors of TNF-alpha, including soluble TNF receptors (etanercept) (Goldenberg, Clin Ther, 21:75–87, 1999) and anti-TNF-alpha antibody (infliximab) (Luong et al., Ann Pharmacother, 34:743–60, 2000), have recently been approved by the U.S. Food and Drug Administration (FDA) as agents for the treatment of rheumatoid arthritis.

Elevated levels of TNF-alpha have also been implicated in many other disorders and disease conditions, including cachexia (Fong et al., Am J Physiol, 256:R659–65, 1989), septic shock syndrome (Tracey et al., Proc Soc Exp Biol Med, 200:233–9, 1992), osteoarthritis (Venn et al., Arthritis Rheum, 36:819–26, 1993), inflammatory bowel disease such as Crohn's disease and ulcerative colitis (Murch et al., Gut, 32:913–7, 1991), Behcet's disease (Akoglu et al., J Rheumatol, 17:1107–8, 1990), Kawasaki disease (Matsubara et al., Clin Immunol Immunopathol, 56:29–36, 1990), cerebral malaria (Grau et al., N Engl J Med, 320:1586–91, 1989), adult respiratory distress syndrome (Millar et al., Lancet 2:712–4, 1989), asbestosis and silicosis (Bissonnette et al., Inflammation, 13:329–39, 1989), pulmonary sarcoidosis (Baughman et al., J Lab Clin Med, 115:36–42, 1990), asthma (Shah et al., Clin Exp Allergy, 25:1038–44 , 1995), AIDS (Dezube et al., J Acquir Immune Defic Syndr, 5:1099–104, 1992), meningitis (Waage et al., Lancet, 1:355–7, 1987), psoriasis (Oh et al., J Am Acad Dermatol, 42:829–30, 2000), graft versus host reaction (Nestel et al., J Exp Med, 175:405–13, 1992), multiple sclerosis (Sharief et al., N Engl J Med, 325:467–72, 1991), systemic lupus erythematosus (Maury et al., Int J Tissue React, 11:189–93, 1989), diabetes (Hotamisligil et al., Science, 259:87–91, 1993) and atherosclerosis (Bruunsgaard et al., Clin Exp Immunol, 121:255–60, 2000).

It can be seen from the references cited above that inhibitors of TNF-alpha are potentially useful in the treatment of a wide variety of diseases. Compounds that inhibit TNF-alpha have been described in U.S. Pat. Nos. 6,090,817; 6,080,763; 6,080,580; 6,075,041; 6,057,369; 6,048,841; 6,046,319; 6,046,221; 6,040,329; 6,034,100; 6,028,086; 6,022,884; 6,015,558; 6,004,974; 5,990,119; 5,981,701; 5,977,122; 5,972,936; 5,968,945; 5,962,478; 5,958,953; 5,958,409; 5,955,480; 5,948,786; 5,935,978; 5,935,977; 5,929,117; 5,925,636; 5,900,430; 5,900,417; 5,891,883; 5,869,677 and others.

Interleukin-6 (IL-6) is another pro-inflammatory cytokine that exhibits pleiotropy and redundancy of action. IL-6 participates in the immune response, inflammation and hematopoiesis. It is a potent inducer of the hepatic acute phase response and is a powerful stimulator of the hypothalamic-pituitary-adrenal axis that is under negative control by glucocorticoids. IL-6 promotes the secretion of growth hormone but inhibits release of thyroid stimulating hormone. Elevated levels of IL-6 are seen in several inflammatory diseases, and inhibition of the IL-6 cytokine subfamily has been suggested as a strategy to improve therapy for rheumatoid arthritis (Carroll et al., Inflamm Res, 47:1–7, 1998). In addition, IL-6 has been implicated in the progression of atherosclerosis and the pathogenesis of coronary heart disease (Yudkin et al., Atherosclerosis, 148:209–14, 1999). Overproduction of IL-6 is also seen in steroid withdrawal syndrome, conditions related to deregulated vasopressin secretion, and osteoporosis associated with increased bone resorption, such as in cases of hyperparathyroidism and sex-steroid deficiency (Papanicolaou et al., Ann Intern Med, 128:127–37, 1998).

Since excessive production of IL-6 is implicated in several disease states, it is highly desirable to develop compounds that inhibit IL-6 secretion. Compounds that inhibit IL-6 have been described in U.S. Pat. Nos. 6,004,813; 5,527,546 and 5,166,137.

Cyclooxygenase is an enzyme that catalyzes a rate-determining step in the biosynthesis of prostaglandins, which are important mediators of inflammation and pain. The enzyme occurs as at least two distinct isomers, cyclooxygenase-1 (COX-1) and cyclooxygenase-2 (COX-2). The COX-1 isomer is constitutively expressed in the gastric mucosa, platelets and other cells and is involved in the maintenance of homeostasis in mammals, including protecting the integrity of the digestive tract. The COX-2 isomer, on the other hand, is not constitutively expressed but rather is induced by various agents, such as cytokines, mitogens,. hormones and growth factors. In particular, COX-2 is induced during the inflammatory response (DeWitt DL, Biochim Biophys Acta, 1083:121–34, 1991; Seibert et al., Receptor, 4:17–23, 1994.). Aspirin and other conventional non-steroid anti-inflammatory drugs (NSAIDs) are non-selective inhibitors of both COX-1 and COX-2. They can be effective in reducing inflammatory pain and swelling, but since they hamper the protective action of COX-1, they produce undesirable side effects of gastrointestinal pathology. Therefore, agents that selectively inhibit COX-2 but not COX-1 are preferable for treatment of inflammatory diseases. Recently, a diarylpyrazole sulfonamide (celecoxib) that selectively inhibits COX-2 has been approved by the FDA for use in the treatment of rheumatoid arthritis (Luong et al., Ann Pharmacother, 34:743–60, 2000; Penning et al., J Med Chem, 40:1347–65, 1997). COX-2 is also expressed in many cancers and precancerous lesions, and there is mounting evidence that selective COX-2 inhibitors may be useful for treating and preventing colorectal, breast and other cancers (Taketo M M, J Natl Cancer Inst, 90:1609–20, 1999; Fournier et al., J Cell Biochem Suppl, 34:97–102, 2000; Masferrer et al., *Cancer Res.*, 60:1306–11, 2000). In 1999 celecoxib was approved by the FDA as an adjunct to usual care for patients with familial adenomatous polyposis, a condition which, left untreated, generally leads to colorectal cancer.

Compounds that selectively inhibit COX-2 have been described in U.S. Pat. Nos. 5,344,991; 5,380,738; 5,434,178; 5,466,823; 5,474,995; 5,510,368; 5,521,207; 5,521,213; 5,536,752; 5,550,142; 5,552,422; 5,604,260; 5,639,780; 5,643,933; 5,677,318; 5,691,374; 5,698,584; 5,710,140; 5,733,909; 5,789,413; 5,811,425; 5,817,700; 5,849,943; 5,859,257; 5,861,419; 5,905,089; 5,922,742; 5,925,631; 5,932,598; 5,945,539; 5,968,958; 5,981,576; 5,994,379; 5,994,381; 6,001,843; 6,002,014; 6,004,950; 6,004,960; 6,005,000; 6,020,343; 6,034,256; 6,046,191; 6,046,217; 6,057,319; 6,071,936; 6,071,954; 6,077,850; 6,077,868; 6,077,869 and 6,083,969.

The cytokine IL-1 beta also participates in the inflammatory response. It stimulates thymocyte proliferation, fibroblast growth factor activity, and the release of prostaglandin from synovial cells.

Elevated or unregulated levels of the cytokine IL-1 beta have been associated with a number of inflammatory diseases and other disease states, including but not limited to adult respiratory distress syndrome (Meduri et al, Chest 107:1062–73, 1995), allergy (Hastie et al, Cytokine 8:730–8, 1996), Alzheimer's disease (O'Barr et al, J Neuroimmunol 109:87–94, 2000), anorexia (Laye et al, Am J Physio: Regul Integr Comp Physiol 279:R93–8, 2000), asthma (Sousa et al, Thorax 52:407–10, 1997), atherosclerosis (Dewberry et al, Arterioscler Thromb Vasc Biol 20:2394–400, 2000), brain tumors (Ilyin et al, Mol Chem Neuropathol 33:125–37, 1998), cachexia (Nakatani et al, Res Commun Mol Pathol Pharmacol 102:241–9, 1998), carcinoma (Ikemoto et al, Anticancer Res 20:317–21, 2000), chronic arthritis (van den Berg et al, Clin Exp Rheumatol 17: S105–14, 1999), chronic fatigue syndrome (Cannon et al, J Clin Immunol 17:253–61, 1997), CNS trauma (Herx et al, J Immunol 165:2232–9, 2000), epilepsy (De Simoni et al, Eur J Neurosci 12:2623–33, 2000), fibrotic lung diseases (Pan et al, Pathol Int 46:91–9, 1996), fulminant hepatic failure (Sekiyama et al, Clin Exp Immunol 98:71–7, 1994), gingivitis (Biesbrock et al, Monogr Oral Sci 17:20–31, 2000), glomerulonephritis (Kluth et al, J Nephrol 12:66–75, 1999), Guillain-Barre syndrome (Zhu et al, Clin Immunol Immunopathol 84:85–94, 1997), heat hyperalgesia (Opree et al, J Neurosci 20:6289–93, 2000), hemorrhage and endotoxemia (Parsey et al, J Immunol 160:1007–13, 1998), inflammatory bowel disease (Olson et al, J Pediatr Gastroenterol Nutr 16:241–6, 1993), leukemia (Estrov et al, Leuk Lymphoma 24:379–91, 1997), leukemic arthritis (Rudwaleit et al, Arthritis Rheum 41:1695–700, 1998), systemic lupus erythematosus (Mao et al, Autoimmunity 24:71–9, 1996), multiple sclerosis (Martin et al, J Neuroimmunol 61:241–5, 1995), osteoarthritis (Hernvann et al, Osteoarthritis Cartilage 4:139–42, 1996), osteoporosis (Zheng et al, Maturitas 26:63–71, 1997), Parkinson's disease (Bessler et al, Biomed Pharmacother 53:141–5, 1999), POEMS syndrome (Gherardi et al, Blood 83:2587–93, 1994), pre-term labor (Dudley, J Reprod Immunol 36:93–109, 1997), psoriasis (Bonifati et al, J Biol Regul Homeost Agents 11:133–6, 1997), reperfusion injury (Clark et al, J Surg Res 58:675–81, 1995), rheumatoid arthritis (Seitz et al, J Rheumatol 23:1512–6, 1996), septic shock (van Deuren et al, Blood 90:1101–8, 1997), systemic vasculitis (Brooks et al, Clin Exp Immunol 106:273–9, 1996), temporal mandibular joint disease (Nordahl et al, Eur J Oral Sci 106:559–63, 1999), tuberculosis (Tsao et al, Tuber Lung Dis 79:279–85, 1999), viral rhinitis (Roseler et al, Eur Arch Otorhinolaryngol Suppl 1:S61–3, 1995), and pain and/or inflammation resulting from strain, sprain, trauma, surgery, infection or other disease processes.

Since overproduction of IL-1 beta is associated with numerous disease conditions, it is desirable to develop compounds that inhibit the production or activity of IL-1 beta. Methods and compositions for inhibiting IL-1 beta are described in U.S. Pat. Nos. 6,096,728; 6,090,775; 6,083,521; 6,036,978; 6,034,107; 6,034,100; 6,027,712; 6,024,940; 5,955,480; 5,922,573; 5,919,444; 5,905,089; 5,874,592; 5,874,561; 5,874,424; 5,840,277; 5,837,719; 5,817,670; 5,817,306; 5,792,778; 5,780,513; 5,776,979; 5,776,954; 5,767,064; 5,747,444; 5,739,282; 5,731,343; 5,726,148; 5,684,017; 5,683,992; 5,668,143; 5,624,931; 5,618,804; 5,527,940; 5,521,185; 5,492,888; 5,488,032 and others.

It will be appreciated from the foregoing that, while there have been extensive prior efforts to provide compounds for inhibiting, for example, TNF-alpha, IL-1, IL-6, COX-2 or other agents considered responsible for immune response, inflammation or inflammatory diseases, e.g. arthritis, there still remains a need for new and improved compounds for effectively treating or inhibiting such diseases. A principal object of the invention is to provide compounds which are effective for such treatments as well as for the treatment of, for example, insulin resistance, hyperlipidemia, coronary heart disease, multiple sclerosis and cancer.

SUMMARY OF THE INVENTION

In one aspect of the invention, compounds of the following formula I are provided:

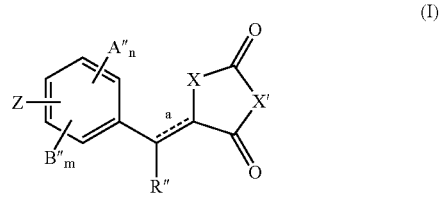

wherein Z is

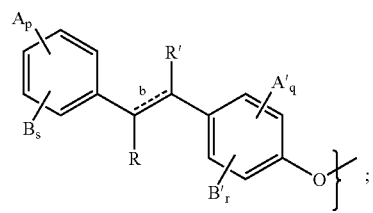

H; A"; B"; or

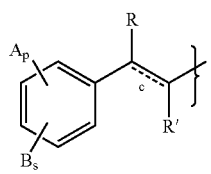

wherein n, m, q and r are independently integers from zero to 4 provided that $n+m \leq 4$, and $q+r \leq 4$; p and s are independently integers from zero to 5 provided that $p+s \leq 5$; a, b and c are double bonds which may be present or absent; when present, the double bonds may be in the E or Z configuration and, when absent, the resulting stereocenters can have the R- or S-configuration;

R, R' and R" are independently H, $C_1$–$C_{20}$ linear or branched alkyl, $C_2$–$C_{20}$ linear or branched alkenyl, —$CO_2Z'$ where Z' is H, sodium, potassium, or other pharmaceutically acceptable counter-ion such as calcium, magnesium, ammonium, tromethamine, and the like; —$CO_2R'''$, —$NH_2$, —NHR''', —$NR_2'''$, —OH, —OR''', halo, substituted $C_1$–$C_{20}$ linear or branched alkyl or substituted $C_2$–$C_{20}$ linear or branched alkenyl, wherein R''' is $C_1$–$C_{20}$ linear or branched alkyl or linear or branched alkenyl;

A, A' and A" are independently H, $C_1$–$C_{20}$ acylamino;
$C_1$–$C_{20}$ acyloxy; $C_1$–$C_{20}$ alkanoyl;
$C_1$–$C_{20}$ alkoxycarbonyl; $C_1$–$C_{20}$ alkoxy;
$C_1$–$C_{20}$ alkylamino; $C_1$–$C_{20}$ alkylcarboxylamino; carboxyl; cyano; halo; hydroxy;

B, B' and B" are independently H;
$C_1$–$C_{20}$ acylamino; $C_1$–$C_{20}$ acyloxy; $C_1$–$C_{20}$ alkanoyl;
$C_1$–$C_{20}$ alkenoyl; $C_1$–$C_{20}$ alkoxycarbonyl;
$C_1$–$C_{20}$ alkoxy; $C_1$–$C_{20}$ alkylamino;
$C_1$–$C_{20}$ alkylcarboxylamino; aroyl, aralkanoyl; carboxyl; cyano; halo; hydroxy;

or A and B together, or A' and B' together, or A" and B" together, may be joined to form a methylenedioxy or ethylenedioxy group; X, X' are independently —NH, —NR''', O or S.

These compounds are useful for treating diabetes, hyperlipidemia and other diseases linked to insulin resistance, such as coronary artery disease and peripheral vascular disease, and also for treating or inhibiting inflammation or inflammatory diseases such as inflammatory arthritides and collagen vascular diseases, which are caused by, for example, cytokines or cyclooxygenase such as TNF-alpha, IL-1, IL-6 and/or COX-2. The compounds are also useful for treating or preventing other diseases mediated by cytokines and/or cyclooxygenase, such as cancer.

Accordingly, the invention also provides a method of treating diabetes and related diseases comprising the step of administering to a subject suffering from a diabetic or related condition a therapeutically effective amount of a compound of Formula I. Additionally, the invention provides a method of treating inflammation or inflammatory diseases or diseases mediated by cytokines and/or cyclooxygenase by administering to a subject in need of such treatment an effective amount of a compound according to Formula I. Other uses will also be evident from this specification.

Pharmaceutical compositions containing a therapeutically effective amount of one or more compounds according to Formula I together with a pharmaceutically or physiologically acceptable carrier, for use in the treatments contemplated herein, are also provided.

BRIEF DESCRIPTION OF THE DRAWINGS

FIGS. 13, 13B, 13C and 13D illustrate the suppression of collageninduced arthritis by using a compound according to the invention.

FIG. 14 illustrates the suppression of experimental allergic encephalomyelitis (EAE) by using a compound according to the invention.

DESCRIPTION OF THE PREFERRED EMBODIMENTS

Figure 1:
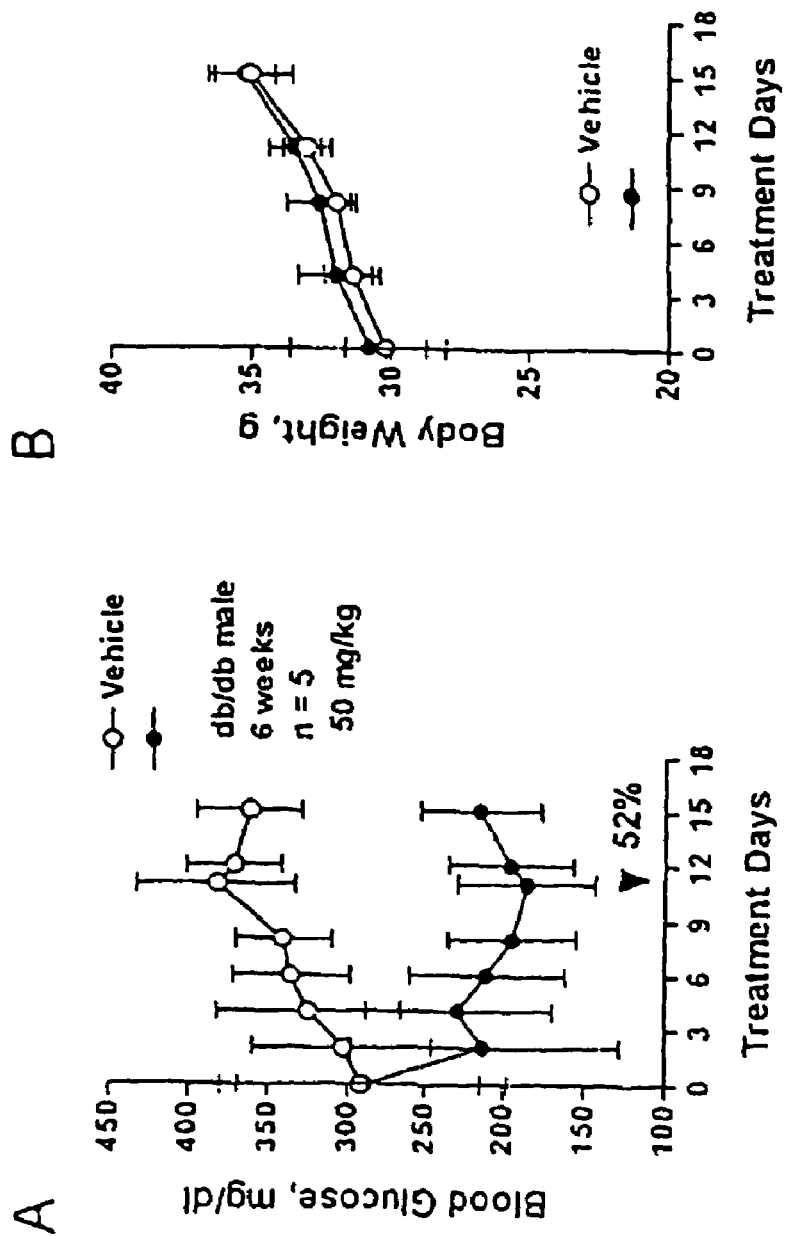
FIGS. 1A and 1B show graphs of the blood glucose levels and body weights, respectively, of db/db (spontaneous diabetic) male mice given a compound according to the invention of a period of 15 days.

A preferred compound according to Formula I is 5-(4-(4-(1-carbomethoxy)-2-(3,5-dimethoxyphenyl)-ethenyl)-phenoxy)-benzyl)-2,4-thiazolidinedione, hereinafter referred to as Compound VIII. However, it will be appreciated that the invention also contemplates the provision and use of other compounds according to Formula I.

The compounds according to the present invention may be combined with a physiologically acceptable carrier or vehicle to provide a pharmaceutical composition, such as, lyophilized powder in the form of tablet or capsule with various fillers and binders. The effective dosage of a compound in the composition can be widely varied as selected by those of ordinary skill in the art and may be empirically determined.

As earlier indicated, the compounds of the invention are useful for the treatment of diabetes, characterized by the presence of elevated blood glucose levels, that is, hyperglycemic disorders such as diabetes mellitus, including both type I and II diabetes, as well as other hyperglycemic related disorders such as obesity, increased cholesterol, hyperlipidemia such as hypertriglyceridemia, kidney related disorders and the like. The compounds are also useful for the treatment of disorders linked to insulin resistance and/or hyperinsulinemia, which include, in addition to diabetes, hyperandrogenic conditions such as polycystic ovary syndrome (Ibanez et al., J. Clin Endocrinol Metab, 85:3526–30, 2000; Taylor A. E., Obstet Gynecol Clin North Am, 27:583–95, 2000), coronary artery disease such as atherosclerosis and vascular restenosis, and peripheral vascular disease. Additionally, the compounds of the present invention are also useful for the treatment of inflammation and immunological diseases that include those mediated by signaling pathways linked to pro-inflammatory cytokines, such as rheumatoid arthritis, multiple sclerosis, inflammatory bowel disease, psoriasis, and contact and atopic dermatitis.

By "treatment", it is meant that the compounds of the invention are administered in an amount which is at least sufficient to, for example, reduce the blood glucose level in a patient suffering from hyperglycemic disorder or to inhibit or prevent the development of pro-inflammatory cytokine or like responses in a patient suffering from inflammatory or immunological disease. In the case of diabetes, the compound is usually administered in the amount sufficient to reduce the blood glucose level, free fatty acid level, cholesterol level, and the like to an acceptable range, where an acceptable range means + or −10%, and usually + or −5% of the normal average blood glucose level and like level of the subject, or sufficient to alleviate the symptoms and/or reduce the risk of complications associated with elevated levels of these parameters. A variety of subjects may be treated with the present compounds to reduce blood glucose levels such as livestock, wild or rare animals, pets, as well as humans. The compounds may be administered to a subject suffering from hyperglycemic disorder using any convenient administration technique, including intravenous, intradermal, intramuscular, subcutaneous, oral and the like. However, oral daily dosage is preferred. The dosage delivered to the host will necessarily depend upon the route by which the compound is delivered, but generally ranges from about 0.1–500 mg/kg human body weight or typically from about 1 to 50 mg/kg human body weight. Generally similar types of administration and dosages are also contemplated when the compounds of the invention are used to treat inflammatory or immunological disease.

The compounds of this invention may be used in formulations using acceptable pharmaceutical vehicles for enteral, or parenteral, administration, such as, for example, water, alcohol, gelatin, gum arabic, lactose, amylase, magnesium stearate, talc, vegetable oils, polyalkylene glycol, and the like. The compounds can be formulated in solid form, e.g., as tablets, capsules, drages and suppositories, or in the liquid form, e.g., solutions, suspensions and emulsions. The preparations may also be delivered transdermally or by topical application.

Representative compounds according to the present invention may be synthesized by the methods disclosed below in Schemes IA, IB, II and III wherein Scheme IA illustrates the preparation of Compound VIII while Schemes IB, II and III describe the synthesis methods more generally.

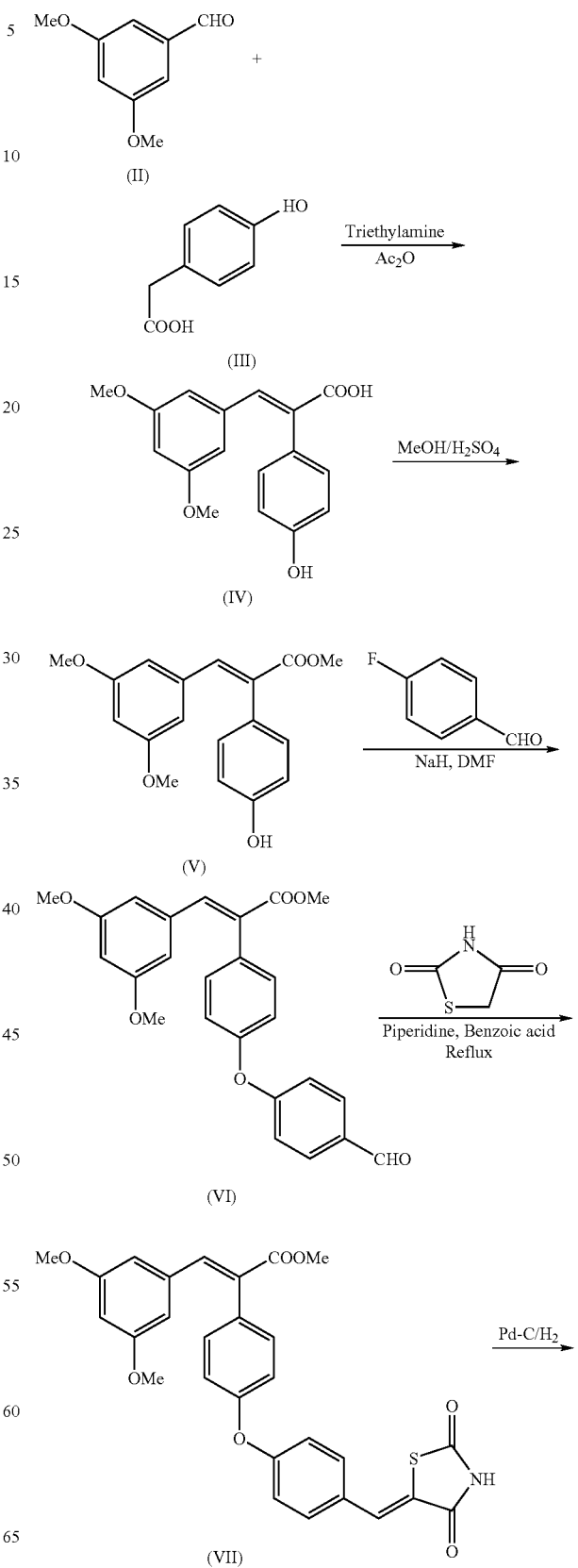

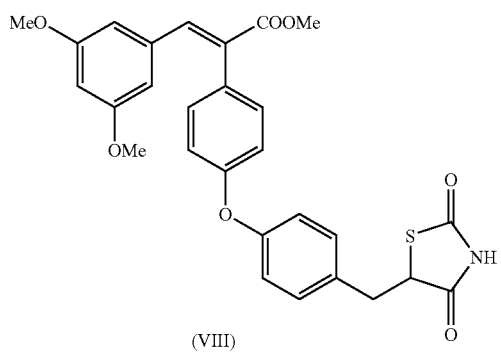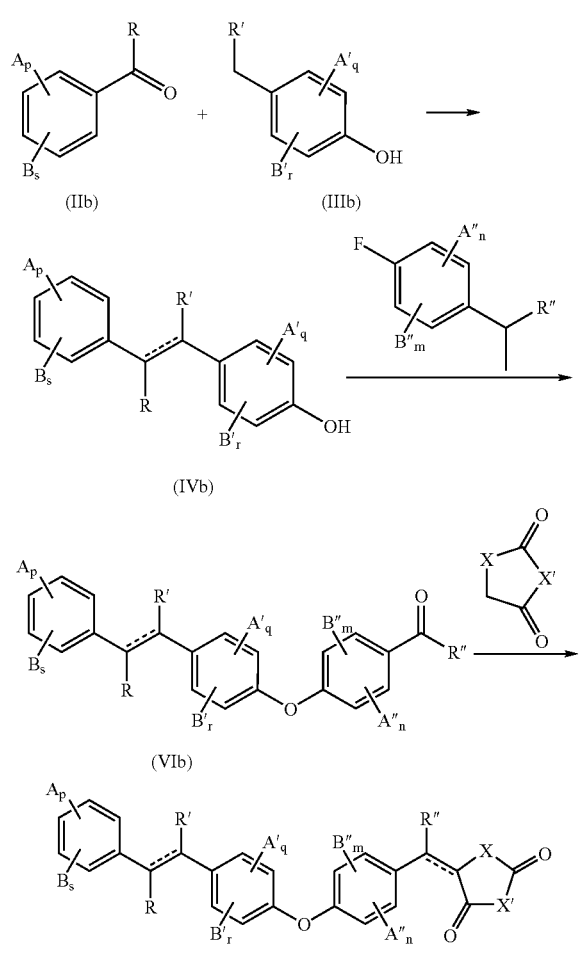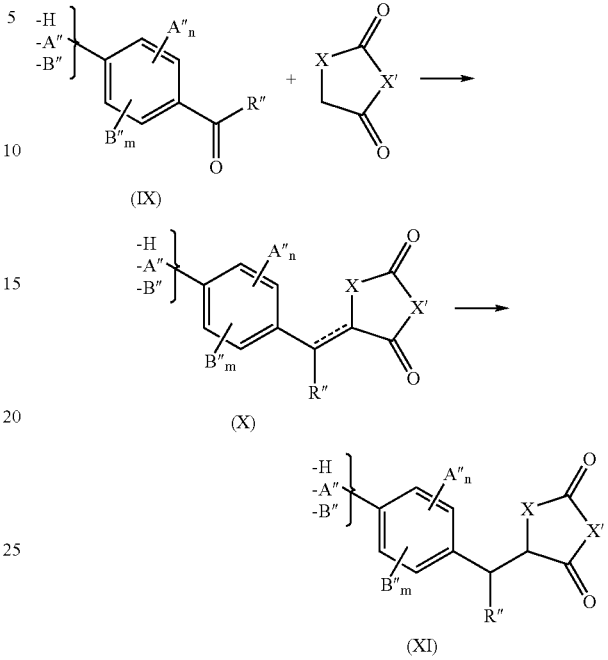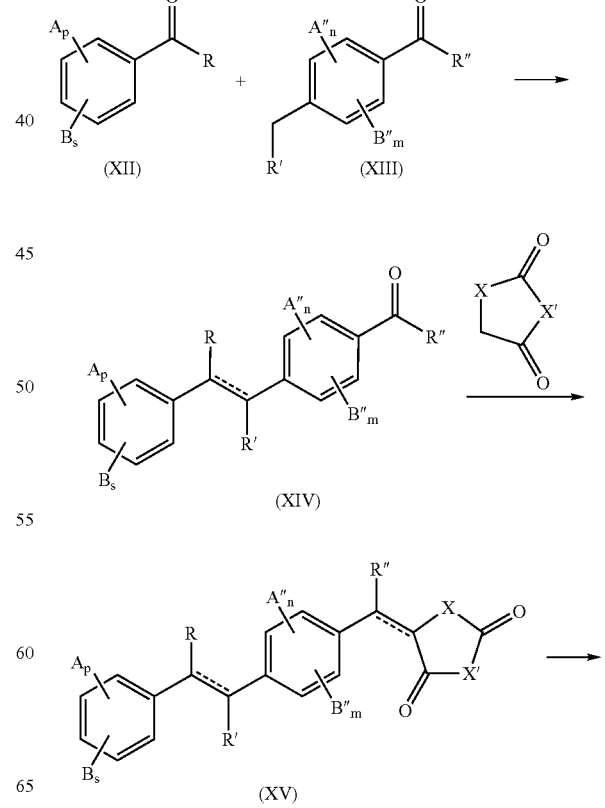

-continued

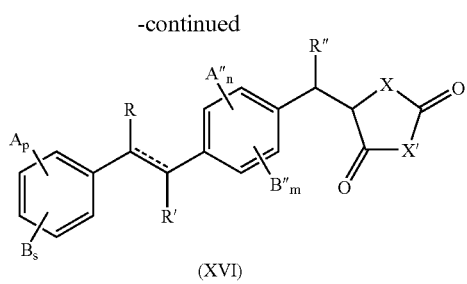

(XVI)

Referring to Scheme IA, the aldehyde (II) and acid (III) may be condensed in acetic anhydride and triethylamine to form the unsaturated acid (IV). After esterification of the acid to provide Compound (V), the phenolic hydroxy group is formed into an ether (VI) with p-fluorobenzaldehyde. The aldehyde (VI) is then condensed with the thiazolidinedione to provide Compound (VII) and the bond exo to the heterocycle in Compound (VII) is reduced with hydrogen to form the object Compound (VIII).

The steps in Scheme IA are generalized in Scheme IB. The general formulas IIb, IIIb, IVb, VIb, VIIb and VIIIb correspond respectively to formulas II, III, IV, VI, VII and VIII in Scheme IA.

In Scheme II, the general synthesis of compounds where Z=H, A" or B" is shown. The aldehyde or ketone (IX) is condensed with the heterocyclic dione to form the bicyclic compound (X), which can be optionally hydrogenated to form the product (XI).

In Scheme III, the general synthesis of the tricyclic products (XV) and (XVI) is shown. The aldehyde or ketone (XII) is condensed with (XIII) to form the bicyclic compound (XIV). The compound (XIV) is condensed with the heterocyclic dione to form the tricyclic product (XV), which can be optionally hydrogenated to (XVI).

In Formula I, $C_1$–$C_{20}$ linear or branched alkyl means groups such as methyl, ethyl, propyl, isopropyl, n-butyl, isobutyl, t-butyl, sec-butyl, isopentyl, neopentyl, etc. The $C_2$–$C_{20}$ linear or branched alkenyl means unsaturated groups such as ethenyl, propenyl, n-butenyl, isobutenyl, including groups containing multiple sites of unsaturation such as 1,3-butadiene, and the like. The halo groups include chloro, fluoro, bromo, iodo. Substituted $C_1$–$C_{20}$ linear or branched alkyl or substituted $C_2$–$C_{20}$ linear or branched alkenyl means that the alkyl or alkenyl groups may be substituted with groups such as halo, hydroxy, carboxyl, cyano, amino, alkoxy, and the like. The $C_1$–$C_{20}$ acylamino or acyloxy group means an oxygen or amino group bonded to an acyl group (RCO) where R can be hydrogen, $C_1$–$C_{20}$ linear or branched alkyl or $C_2$–$C_{20}$ linear or branched alkenyl. Alkenyl groups are —C=C—, where R can be hydrogen, $C_1$–$C_{20}$ linear or branched alkyl or $C_2$–$C_{20}$ linear or branched alkyl. Alkoxycarbonyl means a group ROCO— where R can be hydrogen, $C_1$–$C_{20}$ linear or branched alkyl or $C_2$–$C_{20}$ linear or branched alkenyl. The $C_1$–$C_{20}$ alkyl carboxyl amino group means a group RCON(R)— where R can be independently hydrogen, $C_1$–$C_{20}$ linear or branched alkyl or $C_2$–$C_{20}$ linear or branched alkenyl. Carboxyl is the group $HO_2C$—, and alkanoyl is the group RCO— wherein R is a linear or branched carbon chain. The group aroyl is Ar—CO— wherein Ar is an aromatic group such as phenyl, naphthyl, substituted phenyl, and the like. Aralkanoyl is the group Ar—R—CO— wherein Ar is a aromatic group such as phenyl, naphthyl, substituted phenyl, etc. and R is a linear branched alkyl chain.

As indicated earlier, the compounds of the invention where a, b or c represents a double bond may have either the E or Z configuration. On the other hand, when a, b or c is absent, i.e. a single bond is present, the resulting compounds may be R- and/or S-stereoisomers. The invention contemplates racemic mixtures of such stereoisomers as well as the individual, separated stereoisomers. The individual stereoisomers may be obtained by the use of an optically active resolving agent. Alternatively, a desired enantiomer may be obtained by stereospecific synthesis using an optically pure starting material of known configuration.

The preparation of compound VIII, i.e. 5-(4-(4-(1-carbomethoxy)-2-(3,5-dimethoxy phenyl)-ethenyl)-phenoxy)-benzyl)-2,4-thiazolidinedione, is described below with reference to Scheme IA as shown earlier:

EXAMPLE 1

(a) Synthesis of 3-(3,5-dimethoxy-phenyl)-2-(4-hydroxy-phenyl)-acrylic acid (Compound IV)

To a mixture of 3,5-dimethoxybenzaldehyde (500 g, 3 mol) and p-hydroxyphenyl acetic acid (457 g, 3 mol) was added acetic anhydride (1 L) and triethylamine (420 mL). This non-homogeneous mixture on heating becomes homogeneous at ~70° C. After being stirred at 130–140° C. for 6 h, the mixture was cooled to room temperature. Concentrated HCl (1 L) was added to the reaction mixture slowly in 50 min keeping temp between 20–30° C. The light yellow precipitate obtained was filtered and rinsed with DI water in the Buchner funnel. The solid was dissolved in 3N NaOH (5 L) and stirred for 1 h and filtered. The filtrate was acidified, maintaining a temperature at 25–30° C., with conc. HCl to pH 1. The precipitated product was filtered and washed with water to give crude product. The crude product was recrystallized from MeOH-$H_2O$ then dried at 40° C. for 6 h. Yield: pale yellow solid 428 g (47%). $^1$HNMR (DMSO-$d_6$): δ12.48 (br, 1H), 9.42 (s, 1H), 7.59 (s, 1H), 6.95 (d, J=8.0 Hz, 2H), 6.76 (d, J=8.0 Hz, 2H), 6.35 (t, J=2.2 Hz, 1H), 6.27 (d, J=2.2 Hz, 2H), 3.56 (s, 6H).

(b) Synthesis of 3-(3,5-dithethoxy-phenyl)-2-(4-hydroxy-phenyl)-acrylic acid methyl ester (Compound V)

Methanol (3 L) was added to thoroughly dried Compound IV (427.5 g, 1.42 mol) under argon. To this stirred suspension concentrated sulfuric acid (100 mL) was added and heated at reflux for 20 h under argon. Methanol was evaporated under reduced pressure at 30° C. The residue was taken up in ethyl acetate (3 L) and washed with water (2×1 L), saturated aqueous Na $HCO_3$ (pH 8, 2×1 L), saturated aqueous sodium chloride solution (2×1 L). Organic layer was dried on anhydrous magnesium sulfate, filtered and the solvent was evaporated. The crude product obtained was dried thoroughly under high vacuum and used as such in the next step. Yield: white solid, 433.6 g (97%). $^1$HNMR ($CDCl_3$): δ 7.72 (s, 1H), 7.06 (d, J=7.9 Hz, 2H), 6.77 (d, J=7.9 Hz, 2H), 6.33 (t, J=2.2 Hz, 1H), 6.26 (d, J=2.2 Hz, 2H), 5.74 (s, 1H), 3.81 (s, 3H), 3.60 (s, 6H).

(c) Synthesis of 3-(3,5-dimethoxy-phenyl)-2-[4-(4-formyl-phenoxy)-phenyl]-acrylic acid methyl ester (Compound VI)

Under argon, Compound V (433 g, 1.37 mol) was dissolved in dry DMF (1.6 L) and to this sodium hydride (60% in oil, 60.4 g, 1.51 mol) was added. To the resulting orange solution, p-fluorobenzaldehyde (185 mL, 1.71 mol) was added and heated at 80° C. for 18 h. The reaction mixture was cooled to room temperature, diluted with ethyl acetate (3 L) and extracted with water (3×1 L), then brine (1×1 L). The organic layer was dried over anhydrous sodium sulfate, filtered and solvent was evaporated. The residue was suspended in methanol (3 L) and stirred overnight. The suspension was chilled and then filtered. Solid obtained was dried under vacuum at 40° C. Yield 445 g (77%).

$^1$HNMR (CDCl$_3$): δ 9.94 (s, 1H), 7.86 (d, J=8.6 Hz, 2H), 7.80 (s, 1H), 7.28 (d, J=8.6 Hz, 2H), 7.11 (d, J=2.9 Hz, 2H), 7.08 (d, J=2.9 Hz, 2H), 6.36 (t, J=2.2 Hz, 1H), 6.25 (d, J=2.2 Hz, 2H), 3.83 (s, 3H), 3.63 (s, 6H).

(d) Synthesis of 3-(3,5-dimethoxy-phenyl)-2-{4-[4-(2,4-dioxo-thiazolidin-5-ylidenemethyl)-phenoxy]-phenyl}-acrylic acid methyl ester (Compound VII)

To a stirred suspension of Compound VI (352 g, 0.82 mol) in anhydrous toluene (2.5 L), 2,4-thiazolidinedione (98.6 g, 0.84 mol), benzoic acid (134 g, 1.10 mol) and piperidine (107.4 g, 1.26 mol) was added sequentially and heated at reflux temperature with continuous removal of water with the help of Dean-Stark apparatus for 5 h. Toluene (1 L) was removed from the reaction mixture and the mixture was placed overnight in a 4° C. cold room. Solid separated was filtered off and mother liquor was evaporated to dryness under reduced pressure. The residue obtained was redissolved in a mixture of MeOH-diethylether (1:1, 3 L). Solution on standing overnight at 4° C. yielded more solids. The solid was filtered; both the crops were pooled together and dried overnight in vacuum oven at 40° C. Yield: 362.5 g (86%). $^1$H NMR (DMSO-d$_6$): δ 12.53 (br, 1H), 7.78 (s, 1H), 7.73 (s, 1H), 7.63 (d, J=9.2 Hz, 2H), 7.25 (d, J=9.2 Hz, 2H), 7.15 (d, J=4.3 Hz, 2H), 7.12 (d, J=4.3 Hz, 2H), 6.42 (t, J=2.2 Hz, 1H), 6.27 (d, J=2.2 Hz, 2H ), 3.73 (s, 3H), and 3.59 (s, 6H).

(e) Synthesis of 5-(4-(4-(1-carbomethoxy)-2-(3,5-dimethoxyphenyl)-ethenyl)-phenoxy)-benzyl)-2,4-thiazolidine dione, also called 3-(3,5-dimethoxyphenyl)-2-{4-[4-(2,4-dioxothiazolidin-5-ylmethyl)phenoxy]-phenyl}-acrylic acid methyl ester (Compound VIII)

Compound VII (30 g, 58 mmol) was dissolved in warm dioxane (900 mL), transferred in a 2 L hydrogenation bottle and 10% Pd-C (~50% water, 15 g) was added to this and hydrogenated in a Parr hydrogenator at 60 psi for 24 h. Following this period, an additional 15 g Pd-C was added and hydrogenation was allowed to continue for another 24 h. Catalyst was filtered through a bed of Celite and solvent was evaporated.

The residue was taken up in acetonitrile (500 ml) and adsorbed on C-18 silica (50 g). The adsorbed material was placed on the top of a column containing C-18 reverse phase silica gel (400 g). Column was eluted with CH$_3$CN in H$_2$O (45%, 2 L), CH$_3$CN in H$_2$O (50%, 2 L), CH$_3$CN in H$_2$O (55%, 2 L) to elute the undesired fractions. Fractions were collected with the start of 60% CH$_3$CN in H$_2$O elution for the desired compound. Fractions were mixed on the basis of their HPLC purity. Acetonitrile was evaporated under reduced pressure. Water was removed by lyophilization. Yield: 12 g (40%). White solid; M.P. 126–128° C. $^1$H NMR (DMSO-d$_6$) δ 12.01 (br, 1H), 7.73 (s, 1H), 7.28 (d, J=8.6 Hz, 2H), 7.19 (d, J=8.6 Hz, 2H), 7.02 (d, J=8.6 Hz, 2H), 6.96 (d, J=8.6 Hz, 2H), 6.40 (t, J=2.2 Hz, 1H), 6.27 (d, J=2.2 Hz, 2H), 4.92 (dd, J=9.2 and 4.4 Hz, 1H), 3.73 (s, 3H), 3.57 (s, 6H), 3.37 (dd, J=14.8 and 4.3 Hz, 1H) and 3.12 (dd, J=14.8 and 9.4 Hz, 1H); IR (KBr) $v_{max}$ 3200, 2950, 2850, 1700, 1600, 1500, 1350, 1150, and 850 cm$^{-1}$; EIMS:m/z, 518, [M–H]$^-$ 265, 249, and 113.

Referring to the drawings, Compound VIII was administered in a single oral dose (50 mg/kg body weight) for 1.5 days to db/db male mice as shown in FIG. 1A. A substantial reduction in blood glucose level was observed. There was no increase in body weight in the treatment group as compared to the control treated with the vehicle without the active ingredient, FIG. 1B.

Figure 2:
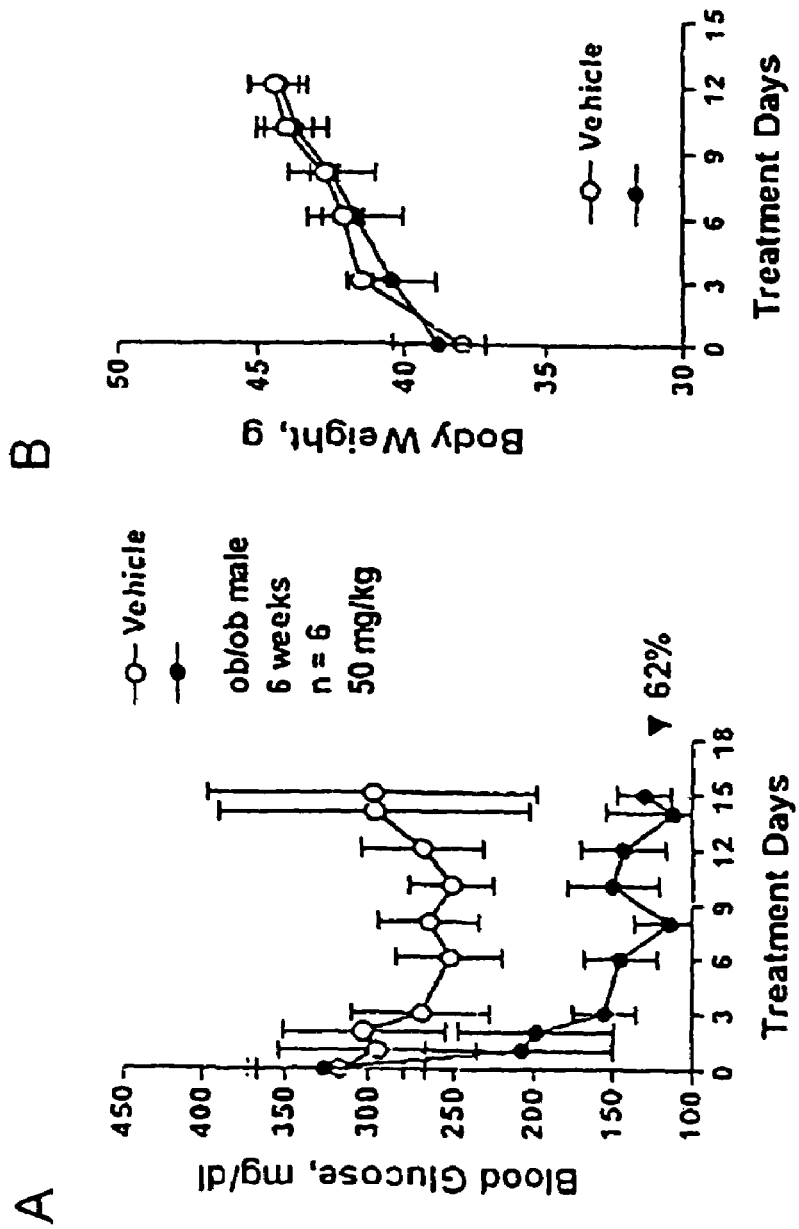
FIGS. 2A and 2B show graphs of the blood glucose levels and body weights of ob/ob (genetically obese and spontaneously diabetic) male mice given a compound according to the invention over a period of 15 days.
Figure 3A:
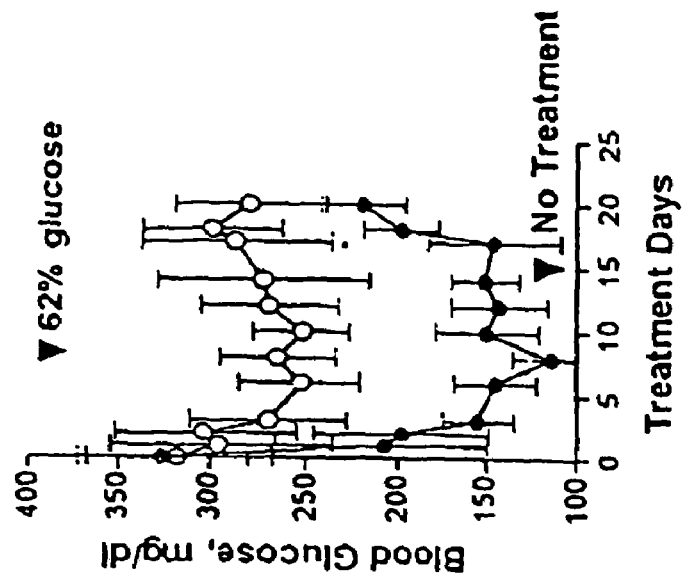
FIGS. 3A and 3B with graphs of blood glucose levels of db/db mice and ob/ob mice, respectively, given a compound according to the invention over a period of 20–25 days.
Figure 3B:
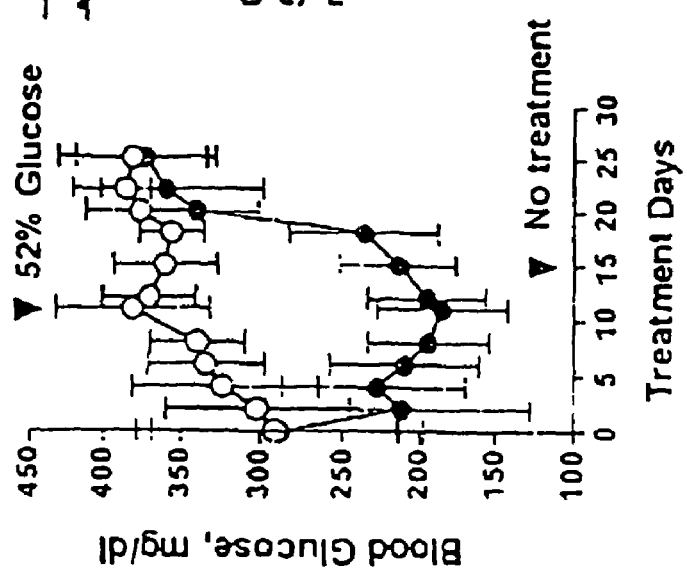
Figure 4:
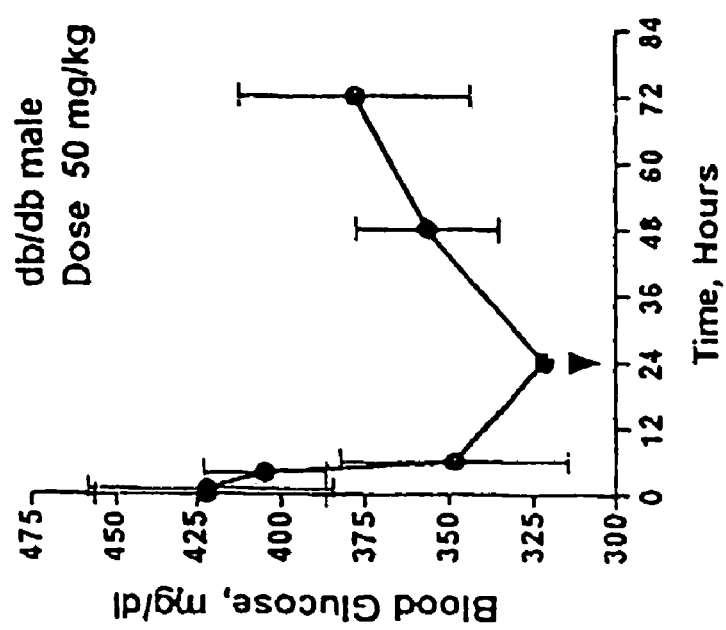
FIG. 4 shows a graph of blood glucose level in db/db male mice over 72 hours following a dosage of the compound.

The compound was orally administered to ob/ob mice with a single oral dose (50 mg/kg body weight). As shown in FIG. 2A, there was a 62% drop in blood glucose level and, similar to db/db mice, there was no significant increase in body weight between the control and the treatment groups as shown in FIG. 2B. This is in contrast to treatment of diabetic animals by thiazolidinedione type compounds which are known to be associated with increase in body weight. See Okuno et al., *J. Clin. Invest.*, 101, 1354–1361 (1998) and Yoshioka et al., *Metabolism*, 42, 75–80 (1993). By stopping treatment after day 15 in both models, there was shown an increase in glucose level as depicted in FIGS. 3A and 3B. The time course of the drug effect is shown in FIG. 4. Oral administration of a single dose of the compound in db/db mice was effective for 24 hours and beyond.

Figure 5:
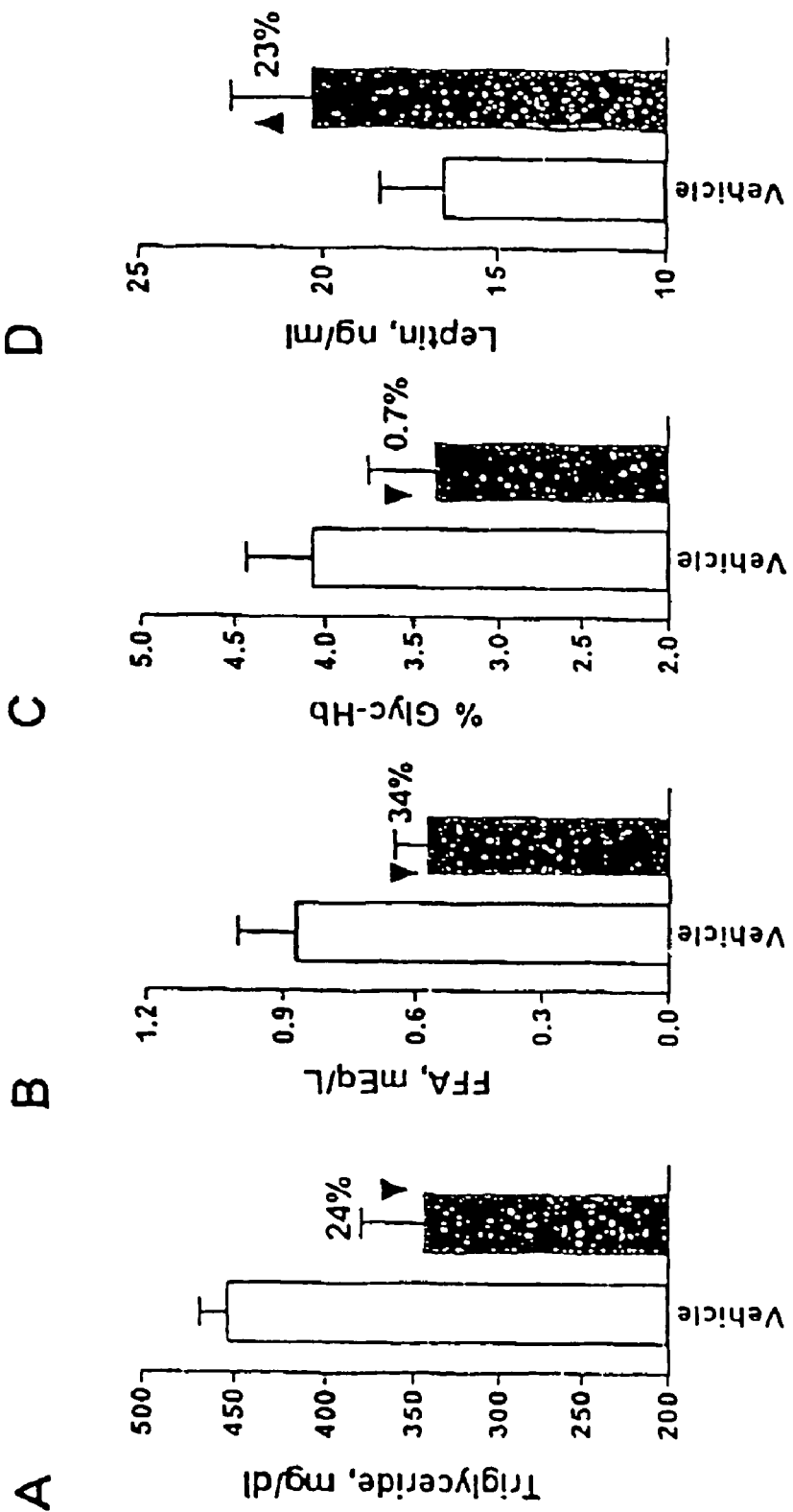
FIGS. 5A, 5B, 5C and 5D show graphs of the triglyceride levels, free fatty acid levels, glyc-Hb levels and leptin levels in serum of the db/db mice treated with a compound according to the present invention.

The triglyceride levels were also measured. Triglycerides, which are esters of fatty acids and glycerol, do not freely circulate in plasma but are bound to proteins and transported as macromolecular complexes called lipoproteins. The triglycerides were measured by the enzymatic method described by McGowen et al., 1983, with a modification to determine the triglyceride levels in db/db and ob/ob mice. There was shown a 24% drop in triglyceride levels in db/db mice (FIG. 5A) after 15 days of treatment with the compound and in ob/ob mice, a 65% decrease in triglyceride as compared to the control (FIG. 6B) after treatment for 10 days.

Figure 6:
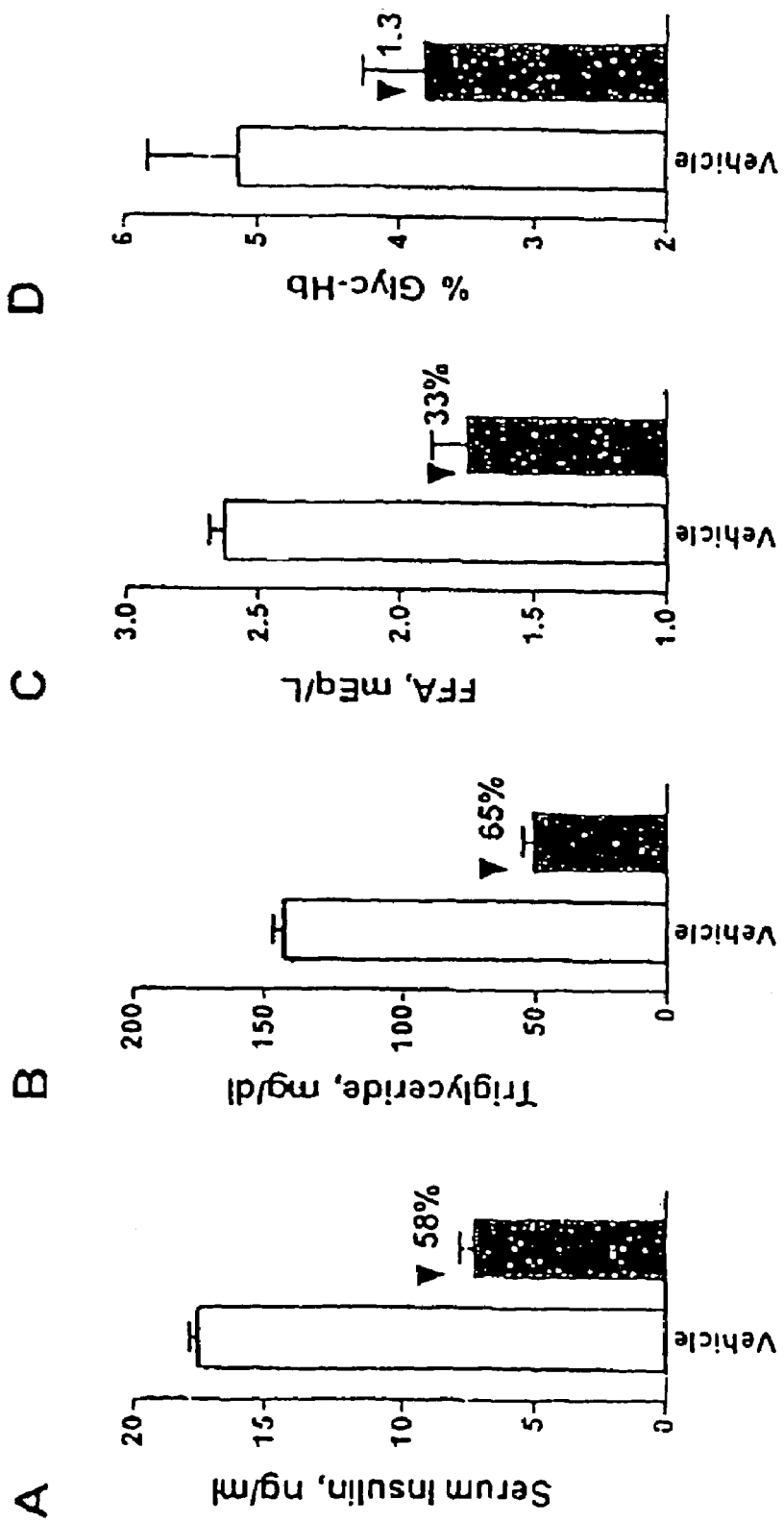
FIGS. 6A, 6B, 6C and 6D are graphs showing the serum insulin levels, triglyceride levels, free fatty acid levels and Glyc-Hb levels of serum of ob/ob mice treated with a compound according to the present invention.

The free fatty acids (FFA) were enzymatically measured using coenzyme A in the presence of acyl CoA synthase (Wako Chemicals USA). The free fatty acid levels in db/db and ob/ob mice treated with the compound were significantly lower compared to the control animals. A 34% drop in FFA levels in db/db mice (FIG. 5B) was shown after 15 days of treatment with the compound. In ob/ob mice, after 10 days of treatment, a lowering of 33% of FFA was shown compared to the control (FIG. 6C).

The percentage of glycohemoglobin (GHb) in blood reflects the average blood glucose concentration. It is a measure of overall diabetic control and can be use to monitor the average blood glucose levels. The glycosylation of hemoglobin occurs continuously in the red blood cells. But since the reaction is non-enzymatic and irreversible, the concentration of glycohemoglobin in a cell reflects the average blood glucose levels seen by the cell during its life. An assay was conducted using affinity chromatography with boronate as described by Abraham et al., *J. Lab. Clin. Med.*, 102, 187 (1983). There is a 0.7% drop in the GHb level in db/db mice (FIG. 5C) after 15 days of treatment with the compound and in ob/ob mice after 14 days of treatment, there is 1.3% decrease (FIG. 6D) in the GHb level compared to the control.

The blood insulin level was measured by ELISA following a standard protocol. A 58% drop of serum insulin in ob/ob mice (FIG. 6A) was shown after 10 days of treatment with the compound, thus, demonstrating its ability to act as an insulin sensitizer.

Obesity is considered a significant risk factor for various adult diseases such as diabetes and cardiac disease. Leptin, an obese gene product, has been identified from the investigation of ob/ob mice, where the leptin is lacking because of a mutation in that gene (Zhiang et al., *Nature*, 372, 425 (1994). Leptin is a protein of about 16 kDa, which is expressed in adipose tissue; and which promotes weight loss by suppressing appetite and stimulating metabolism. It is currently believed that leptin plays a key role in the obesity syndrome. In the db/db mice according to the experiment, the leptin level Was measured by an ELISA, following a standard protocol. After 15 days of treatment with the compound, there is a 23% increase (FIG. 5D) in the serum leptin level compared to the control group.

Figure 7:
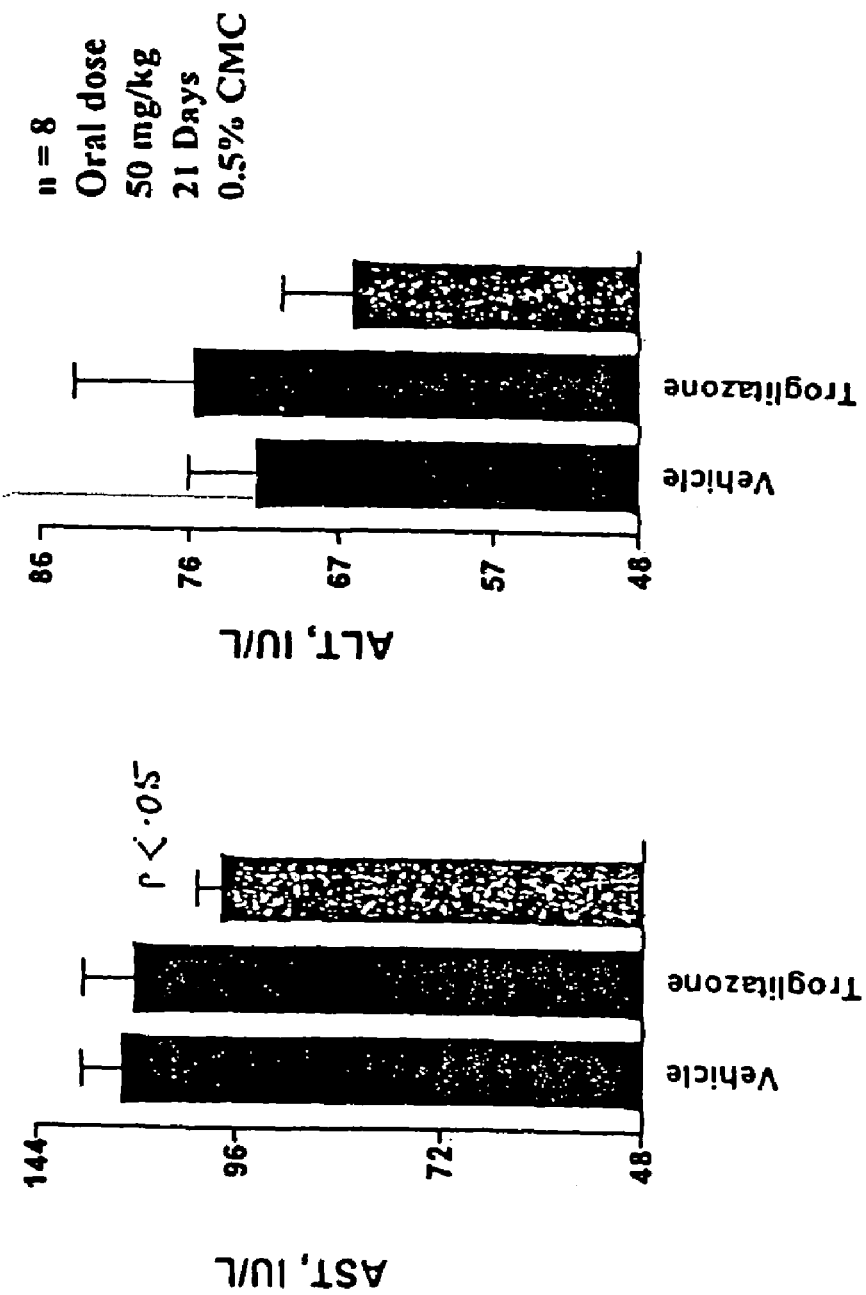
FIGS. 7A and 7B show the assays of liver enzymes in mice 21 days after treatment with a compound according to the invention.

The liver enzymes glutamic oxalacetic transaminase/aspartate aminotransferase (AST/GOT) and glutamic pyruvic transaminase/alanine aminotransferase (ALT/GPT) were assayed in the sera of ob/ob mice after 21 days of treatment (orally, 50 mg/kg) of the test compound. The test was also conducted using troglitazone. These enzyme levels are found to elevate in several kinds of hepatic disorders or liver necrosis. In FIG. 7A, the AST level in the mice was not elevated compared to untreated mice or to mice treated with troglitazone. Similarly, FIG. 7B shows that the ALT level did not elevate compared to untreated mice or mice treated with troglitazone.

Figure 8:
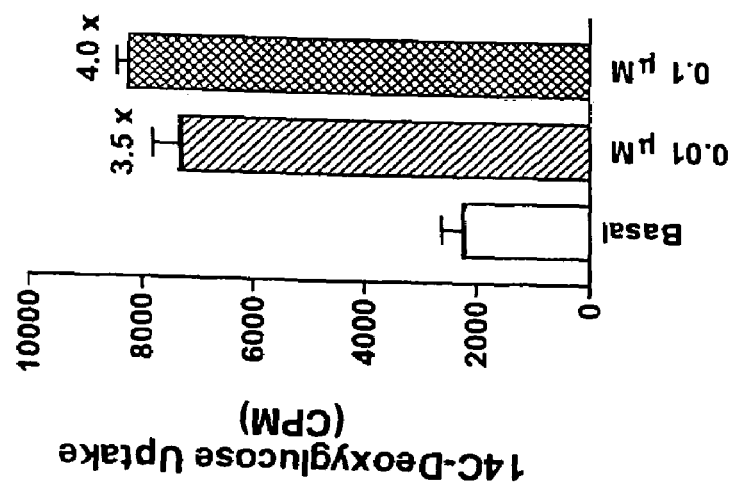
FIG. 8 shows glucose uptake in 3T3-L1 cells for a compound of the invention.

Referring to FIG. 8 glucose uptake in 3T3-L1 differentiated adipocytes was measured after treatment with the test compound. The assay was conducted according to the method of Tafuri, *Endocrinology*, 137, 4706–4712 (1996). The serum-starved cells were treated with the test compound for 48 hours at different concentrations, then washed and incubated in glucose-free media for 30 minutes at 37° C. Then $^{14}$C-deoxyglucose was added and uptake was monitored for 30 minutes under incubation. After washing, the cells were lysed (0.1% SDS) and counted. As shown in FIG. 8, there is a 3.5 to 4-fold increase in glucose uptake at the indicated concentrations of the test compound with respect to basal levels.

Figure 9:
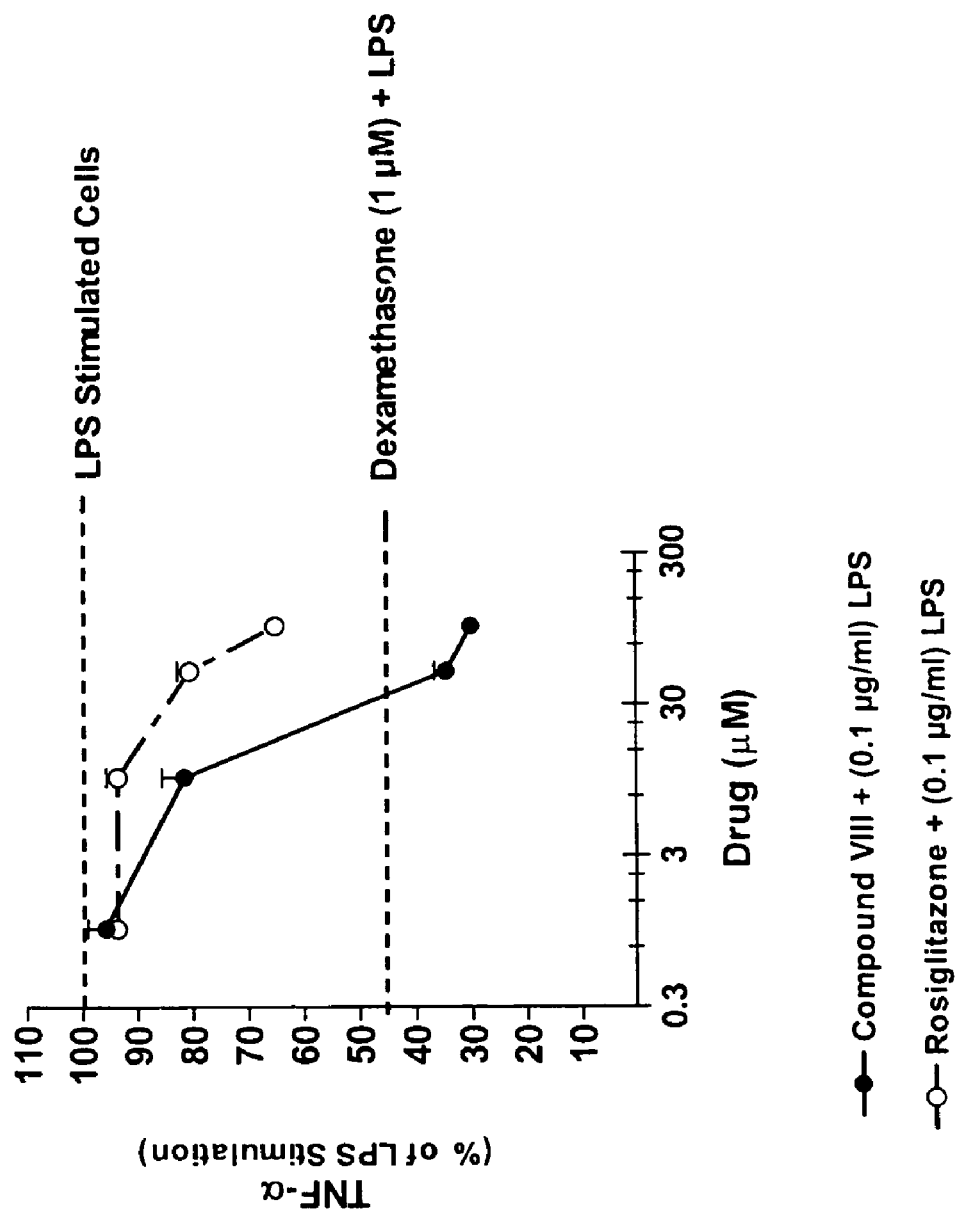
FIG. 9 shows a graph of the comparison of a compound of the invention with rosiglitazone for inhibition of LPS-induced TNF production.

Referring to FIG. 9, RAW cells were preincubated with either Compound VIII or rosiglitazone (0.1, 1, 10, 50 or 100 μM) for 1 hour at 37° C. in RPMI-1640 containing 10% FBS. After 1 hour LPS (0.1 μg/ml) was added and cells were incubated an additional 6 hours. Cell supernatant was then collected, aliquoted and frozen at −70° C., and an aliquot used to determine TNF-alpha concentration by ELISA. Compound VIII was a better inhibitor of TNF-alpha than rosiglitazone.

Figure 10:
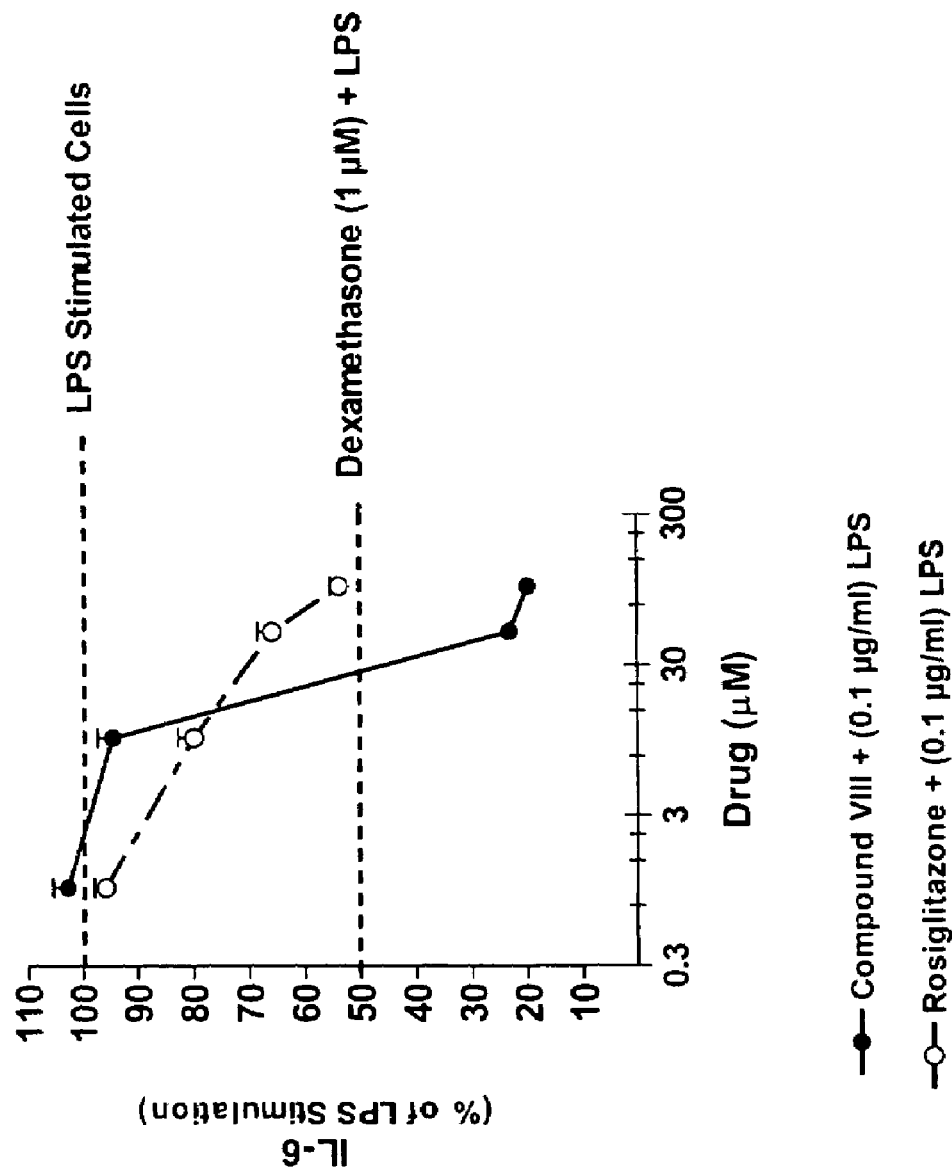
FIG. 10 is a graph of the comparison of a compound of the invention with rosiglitazone for inhibition of LPS-induced IL-6 production.

Referring to FIG. 10, RAW cells were preincubated with either Compound VIII or rosiglitazone (0.1, 1, 10, 50 or 100 μM) for 1 hour at 37° C. in RPMI-1640 containing 10% FBS. After 1 hour LPS (0.1 μg/ml) was added and cells were incubated an additional 6 hours. Cell supernatant was then collected, aliquoted and frozen at −70° C., and an aliquot used to determine the concentration of IL-6 by ELISA. Compound VIII was a better inhibitor of IL-6 than rosiglitazone.

Figure 11:
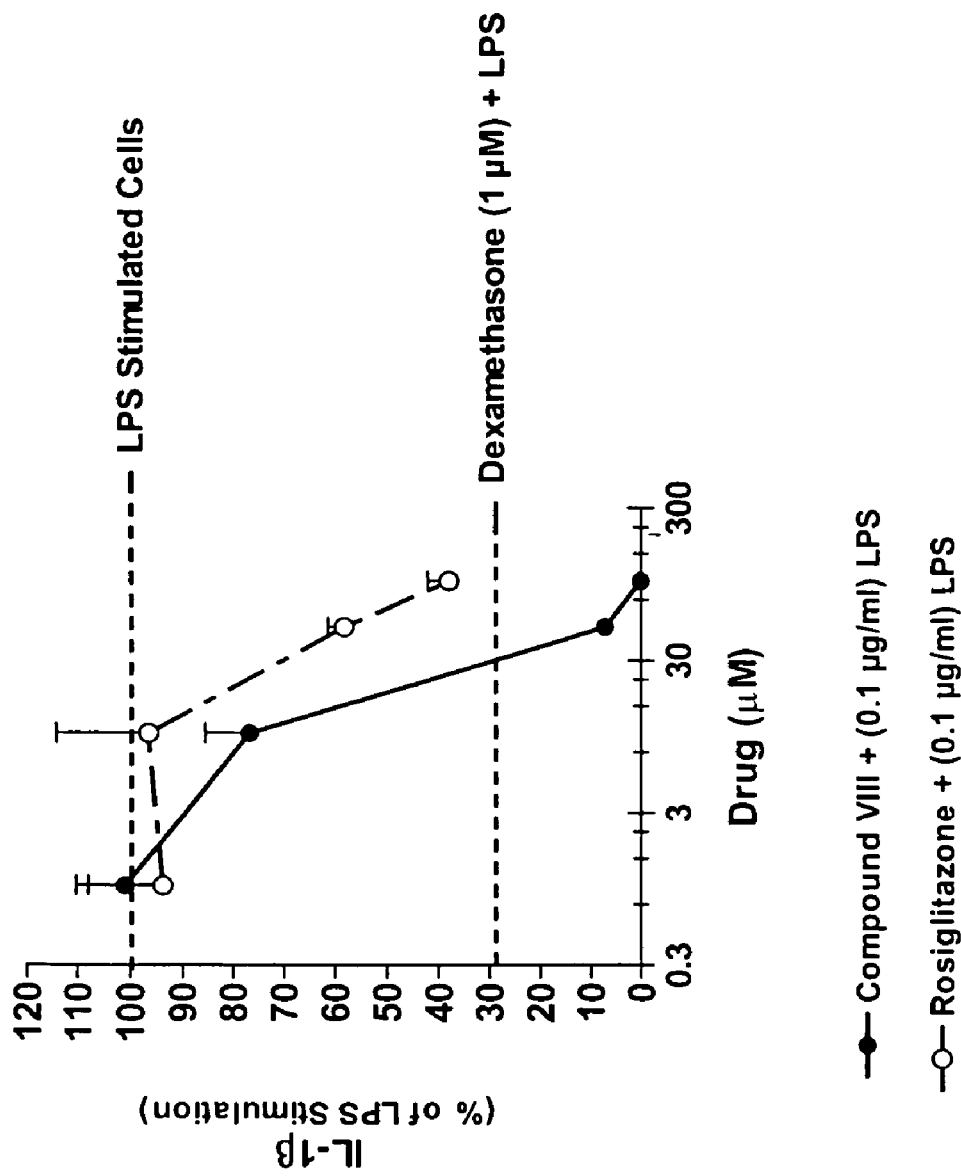
FIG. 11 is a graph of the comparison of a compound of the invention with rosiglitazone for inhibition of LPS-induced IL-1-beta production.

Referring to FIG. 11, RAW cells were preincubated with either Compound VIII or rosiglitazone (0.1, 1, 10, 50 or 100 μM) for 1 hour at 37° C. in RPMI-1640 containing 10% FBS. After 1 hour LPS (0.1 μg/ml) was added and cells were incubated an additional 6 hours. Cell supernatant was then collected, aliquoted and frozen at −70° C., and an aliquot used to determine the concentration of IL-1-beta by ELISA. Compound VIII inhibited IL-1-beta better than rosiglitazone.

Figure 12B:
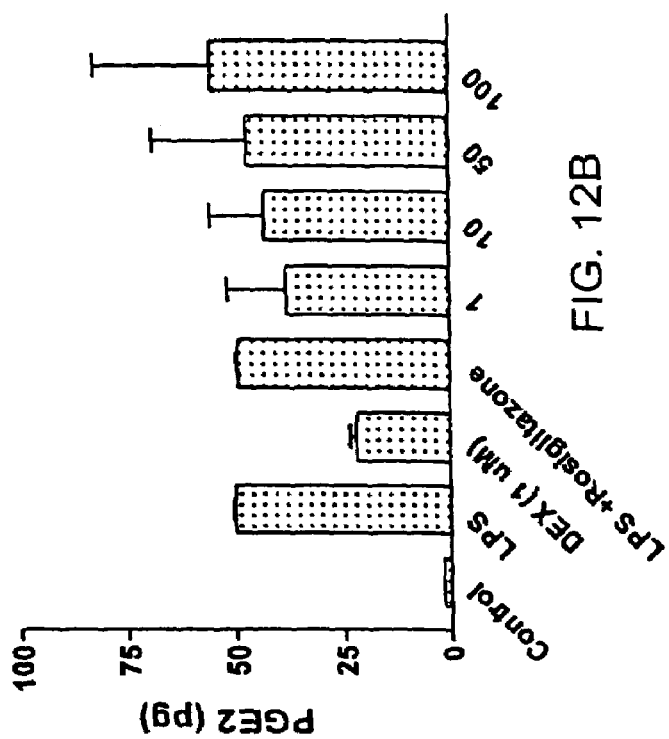
FIGS. 12A and 12B show a comparison of a compound of the invention (FIG. 12A) with rosiglitazone (FIG. 12B) for inhibition of LPS-induced COX-2 activity.
Figure 12A:
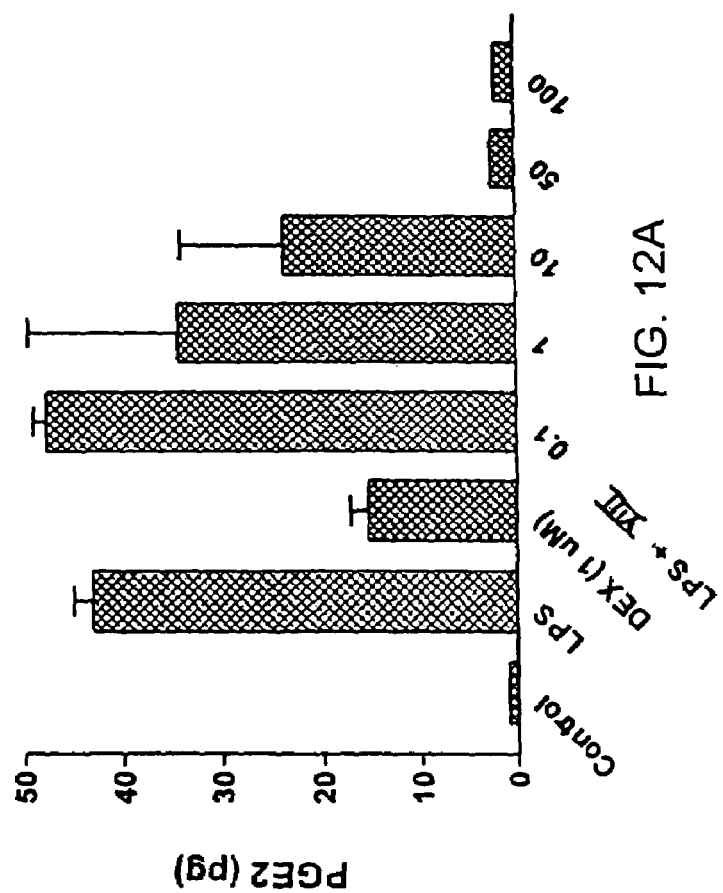

Referring to FIGS. 12A AND 12B, RAW cells were preincubated with either Compound VIII (12A) or rosiglitazone (12B) (0.1, 1, 10, 50 or 100 μM) for 1 hour at 37° C. in RPMI-1640 containing 10% FBS. After 1 hour LPS (0.1 μg/ml) was added and cells were incubated an additional 6 hours. Cell supernatant was then collected, aliquoted and frozen at −70° C., and aliquots used to determine COX-2 and COX-1 activity. Compound VIII, but not rosiglitazone, inhibited the activity of COX-2 (as measured by PGE2 production in a 50 μl sample). Neither compound inhibited COX-1 activity.

The transcription factor NF-kappaB coordinates the activation of many genes involved in the response to pro-inflammatory cytokines, and, therefore, plays a key role in the development of inflammatory diseases. NF-kappaB is activated by phosphorylation of the inhibitory protein IkappaB. To examine the effect of compound VIII on the LPS-stimulated phosphorylation of IkappaB, RAW 264.7 cells were preincubated with vehicle only, 15-deoxy-$\Delta^{12,14}$-prostaglandin $J_2$ (3 μM) as a positive control, compound VIII (3, 10 or 30 μM), or rosiglitazone (3, 10 or 30 μM) for 1 hr. at 37° C. Then, cells were treated with or without LPS (10 ng/ml) plus IFN-gamma (10 U/ml) for 5 min. or 15 min. at 37° C. Cells were then lysed, and the cell lysates (27 μg/lane) were separated by electrophoresis on a 4–20% polyacrylamide gel, blotted onto a nitrocellulose membrane and probed with anti-phospho-IkappaB antibody. The results revealed that compound VIII, but not rosiglitazone, exhibited dose-dependent inhibition of the phosphorylation of IkappaB.

FIGS. 13A–D illustrate the suppression of collagen-induced arthritis by treatment with Compound VIII. Arthritis was induced by intradermal administration of collagen (100 μg/mouse) in complete adjuvant in make DBA/1Lac mice of 7 weeks. The booster (100 μg/mouse) immunization in incomplete adjuvant was given subcutaneously on Day-21. Two days later when arthritic scores were around 1, the animals were divided into two groups. One group received 50 mg/kg dose of Compound VIII orally for 17 days daily. The second group received 10% PEG in water and was used as a vehicle treated group. Body weight (FIG. 13A), Clinical score (FIG. 13B), Joints affected (FIG. 13C) and Paw thickness (FIG. 13D) were monitored 24 hours after the drug administration at different time intervals. As shown in the Figures, the mice treated with Compound VIII showed significantly lower clinical scores, joints affected and paw thickness when compared to the vehicle treated group. There was no change in body weight between the vehicle and the treatment groups.

Experimental allergic encephalomyelitis (EAE) is an autoimmune demyelinating inflammatory disease of the central nervous system. EAE exhibits many of the clinical and pathological manifestations of human multiple sclerosis (MS), and it serves as an animal model to test potential therapeutic agents for MS (Scolding et al, *Prog. Neurobiol.*, 43:143–73, 2000). FIG. 14 illustrates the suppression of EAE by Compound VIII. Active EAE was induced in SJL/J mice essentially according to the method of Owens and Sriram (*Neurol Clin*, 13:51–73, 1995). Naïve mice were immunized subcutaneously with 400 μg each of mouse spinal cord homogenate in complete Freund's adjuvant on day 0 and day 7. Mice were then treated once daily by subcutaneous injection with 50 μg or 200 μg of Compound VIII or with vehicle only. Paralysis was graded according to the numeric scale indicated. As evidenced by the dramatic reduction in clinical score shown in FIG. 14, treatment with the 200 μg dose of Compound VIII was highly effective in ameliorating EAE.

It will be evident from the above that the compounds according to the present invention, as represented by Compound VIII, not only lower blood glucose level, triglyceride level, free fatty acid level, glycohemoglobin and serum insulin, but also raise the leptin level while showing no significant increase in body weight or liver toxicity. The compounds also inhibit TNF-alpha IL-6, IL-1β production and COX-2 activity in vitro and, as shown by FIGS. 13A–13D and 14, the compounds can be used to suppress arthritis and potentially to treat multiple sclerosis, respectively. The properties demonstrated above indicate that the compounds of the invention should be useful in the treatment of disorders associated with insulin resistance, hyperlipidemia, coronary artery disease and peripheral vascular disease and for the treatment of inflammation, inflammatory diseases, immunological diseases and cancer, especially those mediated by cytokines and cyclooxygenase.

While the invention has been exemplified above by reference to the preparation and use of compound VIII, it will be understood that the invention is of broader application consistent with the scope of compounds represented by Formula I. This includes, for example, compound VII, which is not only useful as an intermediate for preparing compound VIII as shown but also demonstrates useful biological activity of its own consistent with the activities of compound VIII.

The synthesis of other compounds representative of the scope of the invention is illustrated by the examples which follow:

EXAMPLE 2

Synthesis of 3-(3,5-dimethoxvphenyl)-2-{4-[4-(2,4-dioxothiazolidin-5-ylmethyl)-phenoxy]-phenyl}-acrylic acid (Compound XVII)

Compound XVII a metabolite of compound VIII, may be prepared by hydrolysis of compound VIII according to the following reaction scheme:

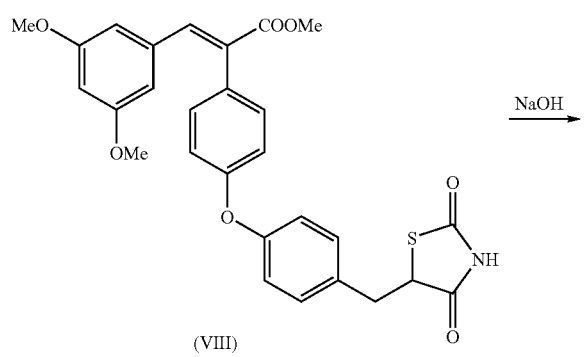

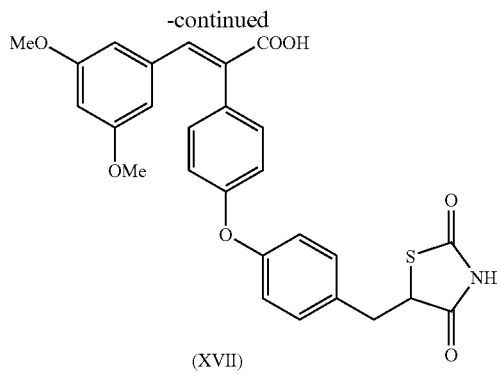

To a stirred, cooled below 10° C., suspension of 3-(3,5-dimethoxyphenyl)-2-{4-[4-(2,4-dioxothiazolidin-5-ylmethyl)-phenoxy]-phenyl}-acrylic acid methyl ester (compound VIII) in methanol (50 mL), aqueous sodium hydroxide (2N, 50 mL) was added and stirred for 15 h at room temperature. The resulting pale yellow solution was cooled to 10° C. and acidified with aqueous HCl (5%, 115 mL). The solid separated was filtered and washed with water (3×30 mL), recrystallized from methanol and dried to give a product characterized as follows:

$^1$H NMR (DMSO-$d_6$) δ7.69 (s, 1H), 7.28 (d, J=8.8 Hz, 2H), 7.19 (d, J=8.8 Hz, 2H), 7.02 (d, J=8.8 Hz, 2H), 6.97 (d, J=8.8 Hz, 2H), 6.41 (t, J=2.4 Hz, 1H), 6.28 (d, J=2.4 Hz, 2H), 4.92 (dd, J=9.2 and 4.4 Hz, 1H), 3.58 (s, 6H), 3.38 (dd, J=14.0 and 4.0 Hz, 1H) and 3.13 (dd, J=14.4 and 9.2 Hz, 1H).

EXAMPLE 3

Synthesis of 3-(3,5-dimethox-phenyl)-2-{4-[4-(2,4-dioxo-thiazolidin-5-ylmethyl)-phenoxy]-phenyl}-acrylamide (Compound XVIII)

Compound XVIII, which may be represented by the formula:

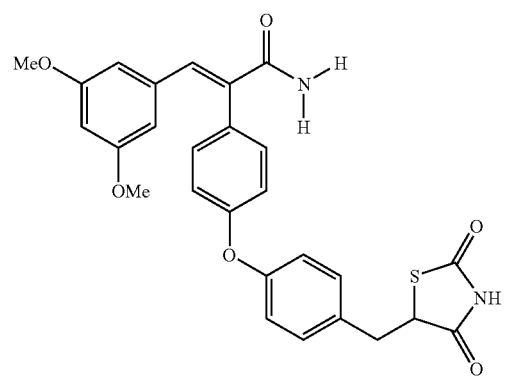

was prepared as follows from compound (XVII):

A clean dry flask with stirbar was charged with compound (XVII) (0.423 g, 0.837 mmol) and dry DMF (10 mL). Then with stirring carbonyidiimidazole (0.271 g, 1.67 mmol) was added and the reaction was heated to 60° C. for 1 h while vented through an oil bubbler. The reaction mixture was then cooled to 0° C. and 2M ammonia in methanol (2.1 mL, 4.2 mmol) was added. The reaction was worked up by partitioning the mixture with 10% citric acid (10 mL), ethyl acetate (50 mL), and water (40 mL). The organic phase was then rinsed sequentially with water (2×30 mL), brine (1×20 mL) and dried with anhydrous magnesium sulfate. Concentration of the organics afforded crude product. The crude product was purified by silica gel chromatography using ethyl acetate-hexanes (1:1) in 1% acetic acid to ethyl acetate-hexanes (3:2) in 1% acetic acid gradient elution. Concentration of the appropriate fractions yielded 200 mg (47%) of the white-light yellow primary amide as a solid. Analysis: $^1$H-NMR, 400 MHz (DMSO-d$_6$): δ12.06 (br, 1H), 7.40 (s, 1H), 7.34 (br, 1H), 7.27 (d, J=8.4 Hz, 2H), 7.18 (d, J=8.8 Hz, 2H), 7.05 (d, J=9.2 Hz, 2H), 6.98 (d, J=8.4 Hz, 2H), 6.93 (br, 1H), 6.36 (m, 1H), 6.20 (s, 1H), 6.19 (s, 1H), 4.91 (dd, J=4.0 Hz, 1H), 3.57 (s, 6H), 3.12 (dd, J=9.2 Hz, 1H).

EXAMPLE 4

Synthesis of 3-(3,5-dimethoxy-phenyl)-2-{4-[4-(2,4-dioxo-thiazolidin-5-ylmethyl)-phenoxy]-phenyl}-N,N-dimethyl-acrylamide (Compound XIX)

Compound (XIX) represented by the formula:

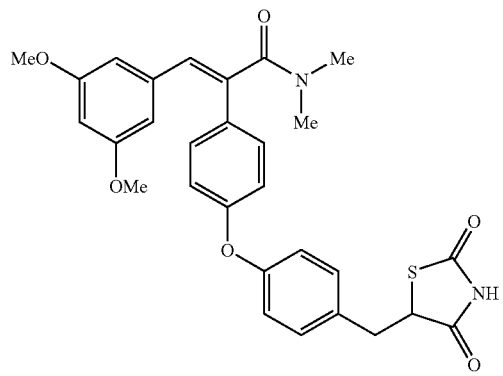

was prepared as follows:

A clean dry flask with stirbar was charged with compound (XVII) (0.422 g, 0.835 mmol) and dry DMF (10 mL). Then with stirring carbonyldiimidazole (0.271 g, 1.67 mmol) was added and the reaction was heated to 60° C. for 1 h while vented through an oil bubbler. The reaction mixture was then cooled to 0° C. and a 2M dimethylamine in THF (2.1 mL, 4.2 mmol) solution was added. The reaction was worked up by partitioning the mixture with 10% citric acid (10 mL), ethyl acetate (50 mL), water (40 mL). The organic phase was then rinsed sequentially with water (2×30 mL), brine (1×20 mL) and dried with anhydrous magnesium sulfate. Concentration of the organics afforded crude product. The crude product was purified by silica gel chromatography using ethyl actate-hexanes (3:2) in 1% acetic acid elution. Concentration of the fractions yielded 381 mg (86%) of the off white tertiary dimethylamide as a solid. Analysis: $^1$H-NMR, 400 MHz (DMSO-d6): δ11.97 (br, 1H), 7.29 (d, J=8.8 Hz, 2H), 7.27 (d, J=8 Hz, 2H), 6.99 (d, J=8.8 Hz), 6.95 (d, J=8.8 Hz, 2H), 6.57 (s, 1H), 6.35 (m, 1H), 6.29 (s, 1H), 6.28 (s, 1H), 4.91 (dd, J=4.4 Hz, 1H), 3.58 (s, 6H), 3.12 (dd, J=9.2 Hz, 1H), 3.05 (br, 3H), 2.91 (s, 3H).

EXAMPLE 5

Synthesis of, 3-(3,5-dimethoxy-phenyl)-2-{4-[4-(2,4-dioxo-thiazolidin-5-ylmethyl)-phenoxy]-phenyl}-N-methoxy,-N-methyl-acrylamide (Compound XX)

Compound (XX) was prepared as follows:

A clean dry flask with stirbar was charged with compound (XVII) (0.450 g, 0.890 mmol) and dry DMF (10 mL). Then, with stirring, carbonyidiimidazole (0.29 g, 1.78 mmol) was added and the reaction was heated to 60° C. for 1 h while vented through an oil bubbler. The reaction mixture was then cooled to 0° C. and N-methyl-N-methoxyhydroxylamine hydrochloride (0.434 g, 4.45 mmol) in water (10 mL) and triethylamine (0.62 mL) was added and stirred overnight. The reaction was worked up by partitioning the mixture with 10% citric acid (10 mL), ethyl acetate (50 mL), and water (40 mL). The organic phase was then rinsed sequentially with water (2×30 mL), brine (1×20 mL) and dried with anhydrous magnesium sulfate. Concentration of the organics afforded crude product. The crude product was purified by silica gel chromatography using ethyl acetate-chloroform (1:5) elution. Concentration of the appropriate fractions yielded 400 mg (82%) of the off-white tertiary N-methyl-N-methoxyamide as a solid. Analysis: $^1$H-NMR, 400 MHz (DMSO-d6): δ12.06 (br, 1H), 7.27 (d, J=9.2 Hz, 2H), 7.26 (d, J=8.8 Hz, 2H), 7.00 (d, J=8.8 Hz), 6.95 (d, J=8.4 Hz, 2H), 6.57 (s, 1H), 6.35 (m, 1H), 6.29 (s, 1H), 6.28 (s, 1H), 4.91 (dd, J=4.4 Hz, 1H), 3.58 (s, 6H), 3.12 (dd, J=9.2 Hz, 1H), 3.05 (br, 3H), 2.91 (s, 3H).

Compound (XX) may be structurally shown as follows:

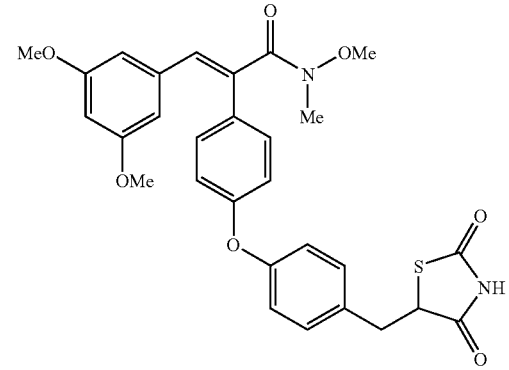

EXAMPLE 6

Synthesis of 3-(3,5-Dimethoxy-phenyl)-2-{4-[4-(2,4-dioxo-thiazolidin-5-ylidenemethyl)-phenoxy]-phenyl}-propionic acid methyl ester, (Compound Vc)

Compound Vc was prepared according to the following reaction scheme:

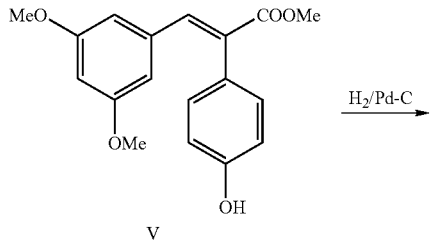

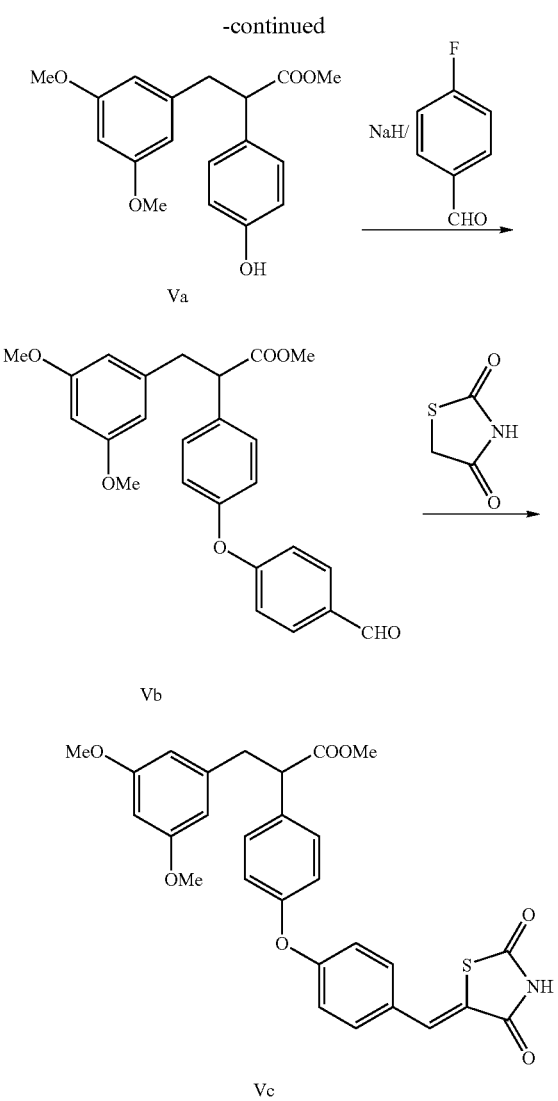

Vc (a) Synthesis of 3-(3,5-Dimethoxy-phenyl)-2-(4-hydroxy-phenyl)-propionic acid methyl ester, (Compound Va)

To a suspension of 3-(3,5-dimethoxy-phenyl)-2-(4-hydroxy-phenyl)-acrylic acid methyl ester (2.1 g) in dioxane (60 mL) 10% palladium on carbon (50% wet, 2.1 g) was added. Hydrogenation was carried out in a Parr shaker at 70 psi for 6.5 h. Catalyst was filtered through a bed of Celite and solvent was evaporated. Yield: quantitative. Analysis: $^1$HNMR (CDCl$_3$): δ7.15 (d, J=8.7 Hz, 2H), 6.74 (d, J=8.7 Hz, 2H), 6.29 (t, J=2.4 Hz, 1H), 6.25 (d, J=2.4 Hz, 2H), 3.78 (t, J=8.7 Hz, 1H), 3.72 (s, 6H), 3.62(s, 3H), 3.31(dd, J=13.5 & 8.4 Hz, 1H), 2.93 (dd, J=13.5 & 6.9 Hz, 1H).

(b) Synthesis of 3-(3,5-Dimethoxy-phenyl)-2-[4-(4-formyl-phenoxy)-phenyl]-propionic acid methyl ester, (Compound Vb)

To a suspension of sodium hydride (60% in oil, 0.25 g, 6.3 mmol) in DMF (2 mL) under argon, Va (2.0 g, 6.3 mmol) in dry DMF (3 mL) was added. To the resulting yellow solution, p-fluorobenzaldehyde (0.68 mL, 6.3 mmol) was added and heated at 80° C. for 18 h. The reaction mixture was cooled to room temperature, water (20 mL) was added and extracted with ethyl acetate (3×50 mL). The organic layer was dried over sodium sulfate, filtered and solvent was evaporated. The crude product was filtered through a small bed of silica gel. Yield: 1.83 g (68.8%). Analysis: $^1$HNMR (DMSO-d$_6$): δ9.91 (s, 1H), 7.84 (d, J=8.7 Hz, 2H), 7.33 (d, J=8.7 Hz, 2H), 7.04 (d, J=5.4 Hz, 2H), 7.01 (d, J=5.4 Hz, 2H), 6.30 (t, J=2.1 Hz, 1H), 6.25 (d, J=2.1 Hz, 2H), 3.86 (t, J=7.8 Hz, 1 Hz), 3.76 (s, 6H), 3.66 (s, 3H), 3.36 (dd, J=12.6 and 8.1 Hz, 1H), 2.97 (dd, J=13.5 & 7.5 Hz, 1H).

(c) Synthesis of 3-(3,5-Dimethoxy-phenyl)-2-{4-[4-(2,4-dioxo-thiazolidin-5-ylidenemethyl)-phenoxy]-phenyl}-propionic acid methyl ester, (Compound Vc)

To a stirred suspension of Vb (1.81 g, 4.3 mmol) in anhydrous toluene (25 mL), 2,4-thiazolidinedione (0.56 g, 4.74 mmol), benzoic acid (0.68 g, 5.60 mmol) and piperidine (60 mL, 6.03 mmol) was added sequentially and heated at reflux temperature with continuous removal of water with the help of Dean-Stark apparatus for 2 h. Solvent was evaporated to dryness under reduced pressure. The residue obtained was purified by silica gel chromatography, eluted with hexane-ethyl acetate (1:1) to yield Vc. Yield: 1.82 g (81.3%) Analysis: $^1$H NMR.(DMSO-d$_6$): δ12.53 (br, 1H), 7.76 (s, 1H), 7.60 (d, J=8.7 Hz, 2H), 7.35 (d, J=8.7 Hz, 2H), 7.07 (d, J=4.8 Hz, 2H), 7.03 (d, J=4.8 Hz, 2H), 6.33–6.28 (m, 3H), 4.01 (t, J=7.5 Hz, 1H), 3.66 (s, 6H), 3.56 (s, 3H), 3.22 (dd, J=13.8 & 8.4 Hz, 1H), 2.90 (dd, J=13.5 & 7.2 Hz, 1H).

EXAMPLE 7

Other specific compounds representative of the invention include the following:

(a) 3-(3,5-dimethoxy-phenyl)-2-{4-[4-(2,4-dioxo-thiazolidin-5-ylidenemethyl)-phenoxy]-phenyl}-acrylic acid methyl ester

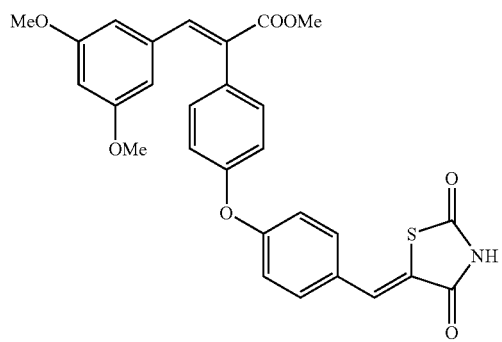

(b) 3-(3,5-dimethoxy-phenyl)-2-{4-[4-(2,4-dioxo-thiazolidin-5-ylmethyl)-phenoxy]-phenyl}-propionic acid methyl ester

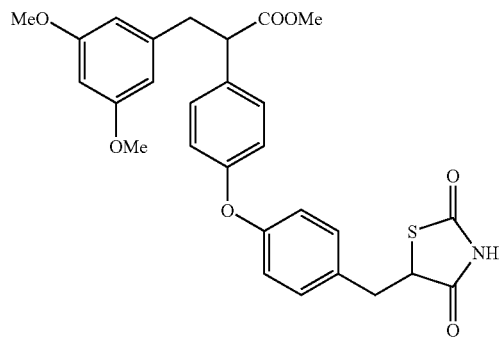

The following additional compounds may also be mentioned as examples of compounds within the broader scope of the invention:

5-(4-fluoro-benzyl)-thiazolidine-2,4-dione

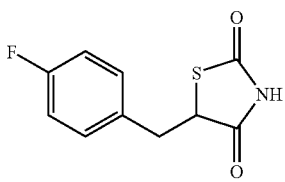

5-(3,5-dimethoxy-benzylidene)-thiazolidine-2,4-dione

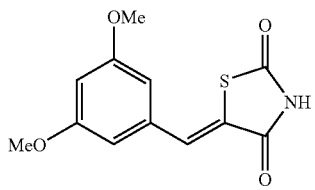

5-(3,5-dimethoxy-benzyl)-thiazolidine-2,4-dione

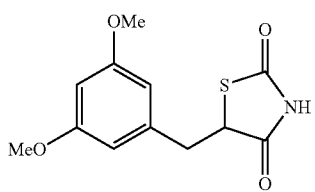

It will be appreciated that various modifications may be made in the invention as described above and as defined in the following claims wherein:

What is claimed is:

1. A compound represented by the following formula 1:

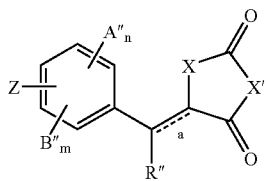

[1]

wherein Z is

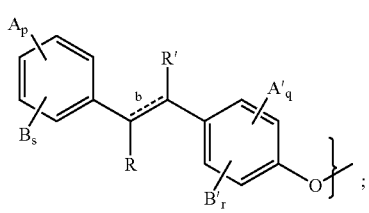

n, m, q and r independently represent integers from zero to 4 provided that $n+m \leq 4$ and $q+r \leq 4$; p and s independently represent integers from zero to 5 provided that $p+s \leq 5$; a and b represent double bonds which may be present or absent; when present, the double bonds may be in the E or Z configuration and, when absent, the resulting stereocenters may have the R- or S-configuration;

R and R' each independently represent a hydrogen atom; linear or branched $C_1$–$C_{20}$ alkyl; linear or branched $C_2$–$C_{20}$ alkenyl; —$CO_2Z'$; —$CO_2R'''$; —$NH_2$; —NHR'''; —$NR_2'''$; —OH; —OR'''; —$CONR_2''''$; halogen atom; optionally substituted linear or branched $C_1$–$C_{20}$ alkyl; optionally substituted linear or branched $C_2$–$C_{20}$ alkenyl;

R'' independently represents a hydrogen atom; linear or branched $C_1$–$C_{20}$ alkyl; linear or branched $C_2$–$C_{20}$ alkenyl; —$CO_2Z'$; —$CO_2R'''$; —$NH_2$; —NHR'''; —$NR_2'''$; —OH; —OR'''; halogen atom; optionally substituted linear or branched $C_1$–$C_{20}$ alkyl; optionally substituted linear or branched $C_2$–$C_{20}$ alkenyl;

R''' independently represents a linear or branched $C_1$–$C_{20}$ alkyl; or linear or branched $C_2$–$C_{20}$ alkenyl;

R'''' independently represents a hydrogen atom; optionally substituted $C_1$–$C_{20}$ alkyl; or optionally substituted $C_1$–$C_{20}$ alkoxy;

Z' represents a hydrogen atom or a pharmaceutically acceptable counter-ion;

A, A' and A'' each independently represent a hydrogen atom; $C_1$–$C_{20}$ acylamino; $C_1$–$C_{20}$ acyloxy; $C_1$–$C_{20}$ alkanoyl; $C_1$–$C_{20}$ alkoxycarbonyl; $C_1$–$C_{20}$ alkoxy; $C_1$–$C_{20}$ alkylamino; $C_1$–$C_{20}$ alkylcarboxylamino; carboxyl; cyano; halo; or hydroxy;

B, B' and B'' each independently represent; $C_2$–$C_{20}$ alkenoyl; aroyl; or aralkanoyl;

or A and B jointly, A' and B' jointly, or A'' and B'' jointly, independently represent a methylenedioxy or ethylenedioxy group; and X and X' independently represent >NH, >NR''', —O—, or —S—.

2. A compound represented by the following formula 1:

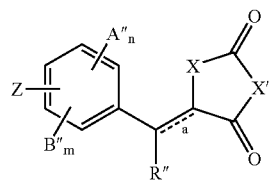

wherein Z is

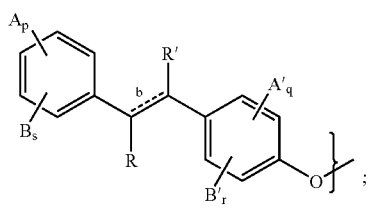

n, m, q and r independently represent integers from zero to 4 provided that n+m≦4 and q+r ≦4; p and s independently represent integers from zero to 5 provided that p+s ≦5; a and b represent double bonds which may be present or absent; when present, the double bonds may be in the E or Z configuration and, when absent, the resulting stereocenters may have the R- or S-configuration;

R and R' each independently represent a hydrogen atom; linear or branched $C_1$–$C_{20}$ alkyl; linear or branched $C_2$–$C_{20}$ alkenyl; —$CO_2Z'$; —$CO_2R'''$; —$NH_2$; —NHR'''; —$NR_2'''$; —OH; —OR'''; halogen atom; optionally substituted linear or branched $C_1$–$C_{20}$ alkyl; optionally substituted linear or branched $C_2$–$C_{20}$ alkenyl;

R" independently represents a hydrogen atom; linear or branched $C_1$–$C_{20}$ alkyl; linear or branched $C_2$–$C_{20}$ alkenyl; —$CO_2Z'$; —$CO_2R'''$; —$NH_2$; —NHR'''; —$NR_2'''$; —OH; —OR''';

halogen atom; optionally substituted linear or branched $C_1$–$C_{20}$ alkyl; optionally substituted linear or branched $C_{2-20}$ alkenyl;

R''' independently represents a linear or branched $C_1$–$C_{20}$ alkyl; or linear or branched $C_2$–$C_{20}$ alkenyl Z' represents a hydrogen atom or a pharmaceutically acceptable counter-ion;

A, A' and A" each independently represent a hydrogen atom; $C_1$–$C_{20}$ acylamino; $C_1$–$C_{20}$ acyloxy; $C_1$–$C_{20}$ alkanoyl;$C_{20}$alkoxycarbonyl; $C_1$–$C_{20}$ alkoxy; $C_1$–$C_{20}$ alkylamino; $C_1$–$C_{20}$ alkylcarboxylamino; carboxyl; cyano; halo; or hydroxy;

B, B' and B" each independently represent; $C_2$–$C_{20}$ alkenoyl; aroyl; or aralkanoyl;

or A and B jointly, A' and B' jointly, or A" and B" jointly, independently represent a methylenedioxy or ethylenedioxy group; and X and X' independently represent >NH, >NR''', —O—, or —S—.

3. The compound of claim 1 that is 3-(3,5-dimethoxyphenyl)-2-{4-[4-(2,4-dioxothiazolidin-5-ylmethyl)-phenoxy]-phenyl}-acrylic acid.

4. The compound of claim 1 that is 3-(3,5-dimethoxyphenyl)-2-{4-[4-(2,4-dioxo-thiazolid in-5-ylmethyl)-phenoxy]-phenyl}-acrylamide.

5. The compound of claim 1 that is 3-(3,5-dimethoxyphenyl)-2-{4-[4-(2,4-dioxo-thiazolid in-5ylmethyl)-phenoxy]-phenyl}-N, N-dimethyl-acrylamide.

6. A pharmaceutical composition comprising:

a) a compound represented by the following formula 1:

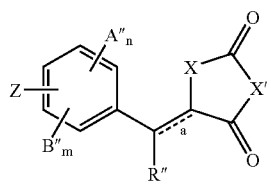

wherein Z is

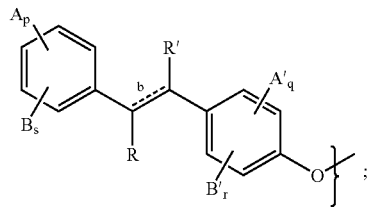

n, m, q and r independently represent integers from zero to 4 provided that n+m≦4 and q+r≦4; p and s independently represent integers from zero to 5 provided that p+s≦5; a and b represent double bonds which may be present or absent; when present, the double bonds may be in the E or Z configuration and, when absent, the resulting stereocenters may have the R- or S-configuration;

R and R' each independently represent a hydrogen atom; linear or branched $C_1$–$C_{20}$ alkyl; linear or branched $C_2$–$C_{20}$ alkenyl; —$CO_2Z'$; —$CO_2R'''$; —$NH_2$; —NHR'''; —$NR_2'''$; —OH; —OR'''; —$CONR_{2''''}$; halogen atom; optionally substituted linear or branched $C_1$–$C_{20}$ alkyl; optionally substituted linear or branched $C_2$–$C_{20}$ alkenyl;

R" independently represents a hydrogen atom; linear or branched $C_1$–$C_{20}$ alkyl; linear or branched $C_2$–$C_2$alkenyl; —$CO_2Z'$; —$CO_2R'''$; —$NH_2$; —NHR'''; —$NR_2'''$; —OH; —OR'''; halogen atom; optionally substituted linear or branched $C_1$–$C_{20}$alkyl; optionally substituted linear or branched $C_2$–$C_{20}$ alkenyl;

R''' independently represents a linear or branched $C_1$–$C_{20}$ alkyl; or linear or branched $C_2$–$C_{20}$ alkenyl;

R"" independently represents a hydrogen atom; optionally substituted $C_1$–$C_{20}$ alkyl; or optionally substituted $C_1$–$C_{20}$ alkoxy;

Z' represents a hydrogen atom or a pharmaceutically acceptable counter-ion;

A, A' and A" each independently represent a hydrogen atom; $C_1$–$C_{020}$ acylamino; $C_1$–$C_{20}$ acyloxy; $C_1$–$C_{20}$ alkanoyl;$C_1C_{20}$alkoxycarbonyl; $C_1$–$C_{20}$ alkoxy; $C_1$–$C_{20}$ alkylamino; $C_1$–$C_{20}$ alkylcarboxylamino; carboxyl; cyano; halo; or hydroxy;

B, B' and B" each independently represent; $C_2$–$C_{20}$ alkenoyl; aroyl; or aralkanoyl;

or A and B jointly, A' and B' jointly, or A" and B" jointly, independently represent a methylenedioxy or ethylenedioxy group; and X and X' independently represent >NH, >NR'''; —O—, or —S—; and b) a physiologically acceptable carrier.

7. A pharmaceutical composition comprising:

a) a compound represented by the following formula 1:

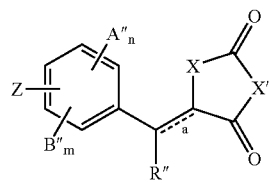

[1]

wherein Z is

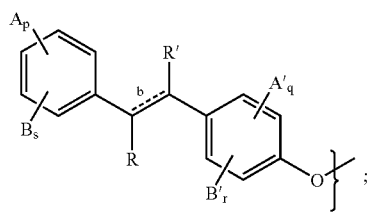

n, m, q and r independently represent integers from zero to 4 provided that n+m≦4 and q+r≦4; p and s independently represent integers from zero to 5 provided that p+s≦5; a and b represent double bonds which may be present or absent; when present, the double bonds may be in the E or Z configuration and, when absent, the resulting stereocenters may have the R- or S-configuration;

R and R' each independently represent a hydrogen atom; linear or branched $C_1$–$C_{20}$ alkyl; linear or branched $C_2$–$C_{20}$ alkenyl; —$CO_2Z'$; —$CO_2R'''$; —$NH_2$; —NHR'''; —$NR_2'''$; —OH; —OR'''; halogen atom; optionally substituted linear or branched $C_1$–$C_{20}$ alkyl; optionally substituted linear or branched $C_2$–$C_{20}$ alkenyl;

R" independently represents a hydrogen atom; linear or branched $C_1$–$C_{20}$ alkyl; linear or branched $C_2$–$C_{20}$ alkenyl; —$CO_2Z'$; —$CO_2R'''$; —$NH_2$; —NHR'''; —$NR_2'''$; —OH; —OR'''; halogen atom; optionally substituted linear or branched $C_1$–$C_{20}$ alkyl; optionally substituted linear or branched $C_2$–$C_{20}$ alkenyl;

R''' independently represents a linear or branched $C_1$–$C_{20}$ alkyl; or linear or branched $C_2$–$C_{20}$ alkenyl;

Z' represents a hydrogen atom or a pharmaceutically acceptable counter-ion;

A, A' and A" each independently represent a hydrogen atom; $C_1$–$C_{20}$ acylamino; $C_1$–$C_{20}$ acyloxy; $C_1$–$C_{20}$ alkanoyl; $C_1$–$C_{20}$ alkoxycarbonyl; $C_1$–$C_{20}$ alkoxy; $C_1$–$C_{20}$ alkylamino; $C_1$–$C_{20}$ alkylcarboxylamino; carboxyl; cyano; halo; or hydroxy;

B, B' and B" each independently represent; $C_2$–$C_{20}$ alkenoyl; aroyl;

or A and B jointly, A' and B' jointly, or A" and B" jointly, independently represent a methylenedioxy or ethylenedioxy group; and X and X' independently represent >NH, >NR''', —O—, or —S—; and b) a physiologically acceptable carrier.

8. The pharmaceutical composition of claim 6, wherein said compound represented by formula I is 3-(3,5-dimethoxyphenyl)-2-{4-[4-(2,4-dioxothiazolidin-5-ylmethyl)-phenoxy]-phenyl}-acrylic acid.

9. The pharmaceutical composition of claim 6, wherein said compound represented by formula I is 3-(3,5-dimethoxy-phenyl)-2-{4-[4-(2,4-dioxothiazolidin-5-ylmethyl)-phenoxy]-phenyl}-acrylamide.

10. The pharmaceutical composition of claim 6, wherein said compound represented by formula I is 3-(3,5-dimethoxy-phenyl)-2-{4-[4-(2,4-dioxothiazolidin-5ylmethyl)-phenoxy]-phenyl}-N,N-dimethyl-acrylamide.

11. A compound represented by the following formula 1:

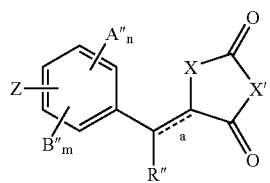

[1]

wherein Z is

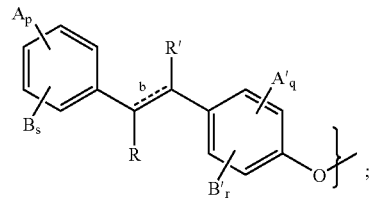

n, m, q and r independently represent integers from zero to 4 provided that n+m≦4 and q+r≦4; p and s independently represent integers from zero to 5 provided that p+s ≦5; a and b represent double bonds which may be present or absent; when present, the double bonds may be in the E or Z configuration and, when absent, the resulting stereocenters may have the R- or S-configuration;

R and R' each independently represent a hydrogen atom; linear or branched $C_1$–$C_{20}$ alkyl; linear or branched $C_2$–$C_{20}$ alkenyl; —$CO_2Z'$; —$CO_2R'''$; —$NH_2$; —NHR'''; —$NR_2'''$; —OH; —OR'''; —$CONR_2''''$; halogen atom; optionally substituted linear or branched $C_1$–$C_{20}$ alkyl; optionally substituted linear or branched $C_2$–$C_{20}$ alkenyl;

R" independently represents a hydrogen atom; linear or branched $C_{1-20}$ alkyl; linear or branched $C_2$–$C_{20}$ alkenyl; —$CO_2Z'$; —$CO_2R'''$; —$NH_2$; —NHR'''; —$NR_2'''$; —OH; —OR'''; halogen atom; optionally substituted linear or branched $C_1$–$C_{20}$ alkyl; optionally substituted linear or branched $C_2$–$C_{20}$ alkenyl;

R''' independently represents a linear or branched $C_1$–$C_{20}$ alkyl; or linear or branched $C_2$–$C_{20}$ alkenyl;

R'''' independently represents a hydrogen atom; methyl; or methoxy;

Z' represents a hydrogen atom or a pharmaceutically acceptable counter-ion;

A, A' and A" each independently represent a hydrogen atom; $C_1$–$C_{20}$ acylamino; $C_1$–$C_{20}$ acyloxy; $C_1$–$C_{20}$ alkanoyl; $C_1$–$C_{20}$ alkoxycarbonyl; $C_1$–$C_{20}$ alkoxy; $C_1$–$C_{20}$ alkylamino; $C_1$–$C_{20}$ alkylcarboxylamino; carboxyl; cyano; halo; or hydroxy;

B, B' and B" each independently represent; $C_2$–$C_{20}$ alkenoyl; aroyl; or aralkanoyl;

or A and B jointly, A' and B' jointly, or A" and B" jointly, independently represent a methylenedioxy or ethylenedioxy group; and X and X' independently represent >NH, >NR''', —O—, or —S—.

12. A pharmaceutical composition comprising:

a) a compound represented by the following formula 1:

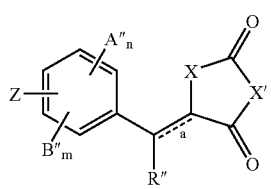

[1]

wherein Z is

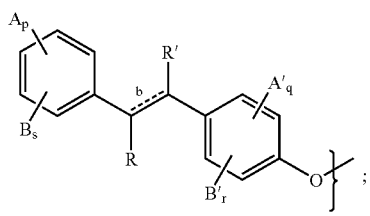

n, m, q and r independently represent integers from zero to 4 provided that n+m≦4 and q+r≦4; p and s independently represent integers from zero to 5 provided that p+s≦5; a and b represent double bonds which may be present or absent; when present, the double bonds may be in the E or Z configuration and, when absent, the resulting stereocenters may have the R- or S-configuration;

R and R' each independently represent a hydrogen atom; linear or branched $C_1$–$C_{20}$ alkyl; linear or branched $C_2$–$C_{20}$ alkenyl; —$CO_2Z'$; —$CO_2R'''$; —$NH_2$; —NHR'''; —$NR_2'''$; —OH; —OR'''; —$CONR_2''''$; halogen atom; optionally substituted linear or branched $C_1$–$C_{20}$ alkyl; optionally substituted linear or branched $C_2$–$C_{20}$ alkenyl;

R" independently represents a hydrogen atom; linear or branched $C_1$–$C_{20}$ alkyl; linear or branched $C_2$–$C_{20}$ alkenyl; —$CO_2Z'$; —$CO_2R'''$; —$NH_2$; —NHR'''; —$NR_2'''$; —OH; —OR'''; halogen atom; optionally substituted linear or branched $C_1$–$C_{20}$ alkyl; optionally substituted linear or branched $C_2$–$C_{20}$ alkenyl;

R''' independently represents a linear or branched $C_1$–$C_{20}$ alkyl; or linear or branched $C_2$–$C_{20}$ alkenyl;

R'''' independently represents a hydrogen atom; methyl; or methoxy;

Z' represents a hydrogen atom or a pharmaceutically acceptable counter-ion;

A, A' and A" each independently represent a hydrogen atom; $C_1$–$C_{20}$ acylamino; $C_1$–$C_{20}$ acyloxy; $C_1$–$C_{20}$ alkanoyl; $C_1$–$C_{20}$ alkoxycarbonyl; $C_1$–$C_{20}$ alkoxy; $C_1$–$C_{20}$ alkylaimino; $C_1$–$C_{20}$ alkylcarboxylamino; carboxyl; cyano; halo; or hydroxy;

B, B' and B" each independently represent; $C_2$–$C_{20}$ alkenoyl; aroyl; or aralkanoyl;

or A and B jointly, A' and B' jointly, or A" and B" jointly, independently represent a methylenedioxy or ethylenedioxy group; and X and X' independently represent >NH, >NR'''—O—, or —S—; and b) a physiologically acceptable carrier.

* * * * *